(12) United States Patent
Yue

(10) Patent No.: US 9,924,972 B2
(45) Date of Patent: Mar. 27, 2018

(54) SYSTEM AND METHOD FOR SPINAL FUSION

(71) Applicant: James J. Yue, Guilford, CT (US)

(72) Inventor: James J. Yue, Guilford, CT (US)

( * ) Notice: Subject to any disclaimer, the term of this patent is extended or adjusted under 35 U.S.C. 154(b) by 122 days.

(21) Appl. No.: 14/807,410

(22) Filed: Jul. 23, 2015

(65) Prior Publication Data

US 2016/0220278 A1    Aug. 4, 2016

Related U.S. Application Data

(60) Provisional application No. 62/111,902, filed on Feb. 4, 2015.

(51) Int. Cl.
| | |
|---|---|
| *A61B 17/70* | (2006.01) |
| *A61B 17/34* | (2006.01) |
| *A61B 17/16* | (2006.01) |
| *A61B 17/17* | (2006.01) |

(52) U.S. Cl.
CPC ...... *A61B 17/7037* (2013.01); *A61B 17/1671* (2013.01); *A61B 17/1757* (2013.01); *A61B 17/3468* (2013.01); *A61B 17/3472* (2013.01); *A61B 17/7076* (2013.01); *A61B 17/7091* (2013.01); *A61B 17/7005* (2013.01)

(58) Field of Classification Search
CPC .......................... A61B 17/70–17/7046; A61B 17/7083–17/7092
See application file for complete search history.

(56) References Cited

U.S. PATENT DOCUMENTS

| | | | |
|---|---|---|---|
| 7,942,909 B2 | 5/2011 | Hammill, Sr. et al. | |
| 8,439,952 B2 | 5/2013 | Geist et al. | |
| 8,535,352 B2 | 9/2013 | Altarac et al. | |
| 8,784,431 B1* | 7/2014 | Harder | A61B 17/7082 606/104 |
| 2006/0241600 A1* | 10/2006 | Ensign | A61B 17/7005 81/52 |
| 2007/0043359 A1 | 2/2007 | Altarac et al. | |
| 2007/0100341 A1* | 5/2007 | Reglos | A61B 17/7004 606/86 A |
| 2007/0239159 A1 | 10/2007 | Altarac et al. | |
| 2007/0270813 A1 | 11/2007 | Garamszegi | |
| 2007/0288026 A1* | 12/2007 | Shluzas | A61B 17/02 606/86 A |
| 2008/0183215 A1* | 7/2008 | Altarac | A61B 17/7005 606/265 |

(Continued)

FOREIGN PATENT DOCUMENTS

| | | |
|---|---|---|
| CN | 203677227 | 7/2014 |
| WO | 2010/024787 | 3/2010 |

*Primary Examiner* — Nicholas Plionis
(74) *Attorney, Agent, or Firm* — Sughrue Mion, PLLC

(57) ABSTRACT

A system for spinal fusion according to exemplary aspects involves a first screw and a second screw to be inserted into a lateral mass, wherein one of the first screw and the second screw comprises a rod configured to form a pivot joint with a tulip of one of the screws. A tulip of the first screw and a tulip of the second screw each comprise at least one slot configured to mate with the rod to thereby connect the first screw and the second screw. A method of exemplary aspects involves implanting a first screw and a second screw and connecting the screw by lowering a rod of one of the screws into a tulip of the other screw.

13 Claims, 31 Drawing Sheets

(56) References Cited

U.S. PATENT DOCUMENTS

| | | |
|---|---|---|
| 2009/0306719 A1* | 12/2009 | Meyer, III ......... A61B 17/7005 606/264 |
| 2010/0228293 A1 | 9/2010 | Courtney et al. |
| 2010/0324599 A1 | 12/2010 | Montello et al. |
| 2011/0087288 A1 | 4/2011 | Stevenson et al. |
| 2012/0215259 A1 | 8/2012 | Cannestra |
| 2013/0123858 A1 | 5/2013 | Attia |
| 2013/0211465 A1 | 8/2013 | Savage |
| 2014/0094857 A1 | 4/2014 | Quevedo et al. |
| 2014/0249581 A1 | 9/2014 | Stachniak |

\* cited by examiner

SYSTEM AND METHOD FOR SPINAL FUSION

CROSS-REFERENCE TO RELATED APPLICATION

This application claims priority under 35 U.S.C. § 119 to U.S. Provisional Application No. 62/111,902, filed on Feb. 4, 2015, the contents of which are herein incorporated by reference in their entirety.

BACKGROUND OF THE INVENTION

1. Field of the Invention

The present invention relates to the field of spinal fusion devices and procedures, and more particularly, relates to a system and method for spinal fusion using a screw and rod device for joining two or more vertebral bodies by posterior cervical fusion.

2. Description of the Related Art

Spinal fusion is a surgical technique used to join two or more vertebrae. Fusing of the spine is used to eliminate pain caused by abnormal motion of the vertebrae by immobilizing the faulty vertebrae themselves, which is usually caused by degenerative conditions.

Posterior cervical fusion is indicated for patients with numerous pathological conditions including traumatic and pathologic fractures, deformity, infection, and for post decompression stabilization. Lateral mass fixation is now the most commonly performed method of stabilization. In order to achieve lateral mass fixation, as well as placement of bone material (autograft and allograft bone/bone substitutes), an open subperiosteal dissection is often performed.

Recently, minimally invasive approaches using tubular retractors have been utilized to perform non-fusion lamino-foraminotomy procedures. For example, the lamino-foraminotomy procedures have been performed using an endoscope. Achieving both a decompression and fusion through the endoscope would be an ideal minimally invasive approach to apply in spinal fusion. However, to date, no such method has been proposed.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above. The present invention provides a system and method for spinal fusion comprising a screw and rod apparatus.

Provided is a spinal fusion apparatus comprising a first screw assembly configured to be inserted into a first lateral mass and second screw assembly configured to be inserted into a second lateral mass, wherein one of the first screw assembly and the second screw assembly comprises a rod configured to form a revolute joint with a tulip of one of the screw assemblies and be lowered into a tulip of the other of the screw assemblies, thereby connecting two vertebral bodies, and a method of performing spinal fusion.

According to an exemplary embodiment of the present invention, there is provided a spinal fusion apparatus comprising a first screw assembly, wherein the first screw assembly comprises a shaft part and a tulip having a slot; and a second screw assembly, wherein the second screw assembly comprises a shaft part, a tulip having a slot, and a rod having a ball, wherein the ball is detachable from the shaft part of the second screw assembly, the ball is configured to form a pivot joint with the tulip of the second screw assembly, and the slot of the first screw assembly and the slot of the second screw assembly are configured to mate with the rod to thereby connect the first screw assembly and the second screw assembly by the rod.

The spinal fusion apparatus may be further configured such that the rod is attachable to the shaft part of the second screw, and the rod is configured to drive the shaft part of the second screw.

The spinal fusion apparatus may be further configured such that the rod comprises the ball at one end and a tip at another end, wherein the tip is configured to mate with a screw driver.

The spinal fusion apparatus may be further configured such that the tip of rod is configured to mate with the screw driver in a snap type latching connection.

The spinal fusion apparatus may be further configured such that the second screw assembly comprises a locking cap having a semi-spherical concave bottom side.

The spinal fusion apparatus may be further configured such that the ball is configured to form a ball-and-socket joint with the tulip of the second screw assembly.

The spinal fusion apparatus may be further configured such that the tulip of the second screw assembly comprises a threaded part configured to mate with a threaded part of the locking cap.

The spinal fusion apparatus may be further configured such that the tulip of the first screw assembly comprises a threaded part configured to mate with a threaded part of the locking cap.

The spinal fusion apparatus may be further configured such that the tulip of the first screw assembly comprises a rounded lower surface configured to engage a rounded upper surface of a head of the shaft part of the first screw assembly.

The spinal fusion apparatus may be further configured such that the tulip of the second screw assembly comprises a rounded lower surface configured to engage a rounded upper surface of a head of the shaft part of the second screw assembly.

The spinal fusion apparatus may further comprise a third screw assembly, wherein the third screw assembly comprises a shaft part and a tulip having a slot.

According to another exemplary embodiment of the present invention, there is provided a hollow cannula comprising: a blade mounted on the cannula, wherein the blade is slidable in a longitudinal direction of the blade; a stabilizing pin; a channel extending parallel to the longitudinal direction of the blade configured to house the stabilizing pin, wherein the stabilizing pin is slidable in the channel, wherein the blade has a substantially planar portion and an extending direction of the channel is offset from a plane of the planar portion.

The cannula may be further configured such that the blade comprises a tab at one end and a tip at the other end, wherein the tip is configured to deploy when the tab is actuated.

The cannula may further comprise a slot at one end of the cannula and a counter torque feature at another end of the cannula.

According to another exemplary embodiment of the present invention, there is provided a method for spinal fusion, the method comprising: positioning a cannula over a first lateral mass; drilling a hole in the first lateral mass by a drill inserted through the cannula; inserting a first screw into the first lateral mass through the cannula; positioning the cannula over a second lateral mass; drilling a hole in the second lateral mass; inserting a second screw into the second lateral mass through the cannula; lowering a rod of one of the first screw and the second screw into a tulip of the other of the first screw and the second screw, thereby connecting the first screw and the second screw.

The method for spinal fusion may further comprise deploying a blade of the cannula into a facet joint.

The method for spinal fusion may further comprise deploying a stabilizing pin of the cannula into one of the first lateral mass and the second lateral mass.

The method for spinal fusion may further comprise inserting an endoscope through the cannula.

The method for spinal fusion may further comprise applying torque to one of the first screw and the second screw by engaging the rod by a slot of the cannula.

The method for spinal fusion may further comprise installing a first locking cap on the first screw and a second locking cap on the second screw.

BRIEF DESCRIPTION OF THE DRAWINGS

The above and other aspects of the present invention will become more apparent from the following description of exemplary embodiments, taken in conjunction with the accompanying drawings of which.

Throughout the drawings, the same drawing reference numerals will be understood to refer to the same elements, features, and structures.

DETAILED DESCRIPTION OF EXEMPLARY EMBODIMENTS

The matters defined in the description such as a detailed construction and elements are provided to assist in a comprehensive understanding of the embodiments of the invention and are merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

Spinal fusion devices of exemplary embodiments set forth herein are implants including a combination screw and flip-rod (a screw-rod). The screw-rod implant comprises a screw with a mobile tulip. Within the tulip, there exists a mobile housing in which a rod having a semi-spherical coupling can fit. One end of the rod has a non-round shape which permits the one end of the rod to sit in a male or female receptacle for turning a threaded shaft of the screw. The other end of the rod also has a non-round portion and thus acts as a drive for engaging with a male or female end of a screw driver. The other end of the rod is partially cannulated and threaded to allow a rod with a threaded end which passes through the shaft of the screw driver into the other end of the rod. Turning the other end of the rod permits turning the screw-rod construct and thus insertion of the screw into a cervical lateral mass. After insertion of the screw, the rod is pulled back by the screw driver and the one end of the rod is disengaged from the female tulip receptacle so that it can float within the tulip, thus effecting a pivot joint such that rotation of the rod is permitted within the tulip. The type of joint may be a revolute joint (that is, having one degree of freedom), a cylindrical joint (having two degrees of freedom), or a spherical joint (having three degrees of freedom). A spherical joint may also be known as a ball-and-socket joint.

Figure 1:
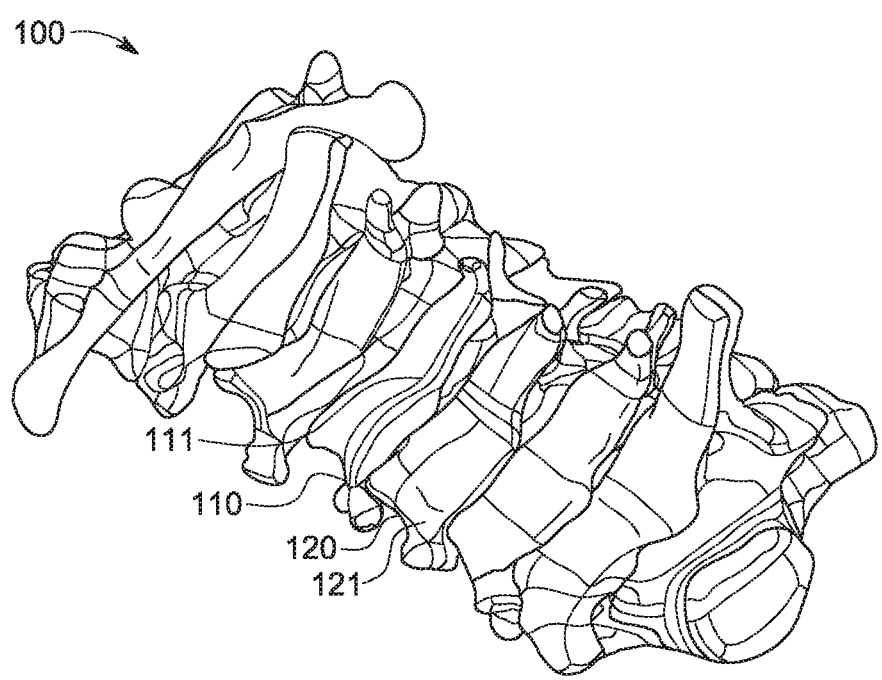
FIG. 1 is an isometric view of a section of cervical vertebrae.

FIG. 1 illustrates an isometric view of a section of cervical vertebrae to which an exemplary screw-rod implant may be applied. The cervical spine 100 consists of a plurality of cervical vertebrae joined by intervertebral disks and a complex network of ligaments. In a segment of cervical vertebrae, there is a superior vertebra 110 having a lateral mass 111 and an adjacent inferior vertebra 120 having a lateral mass 121. In FIG. 1, the lateral mass is labeled on one side of the spinous process, but it is understood that a lateral mass on either side of the vertebra may be selected as the site for lateral mass fixation.

Figure 17:
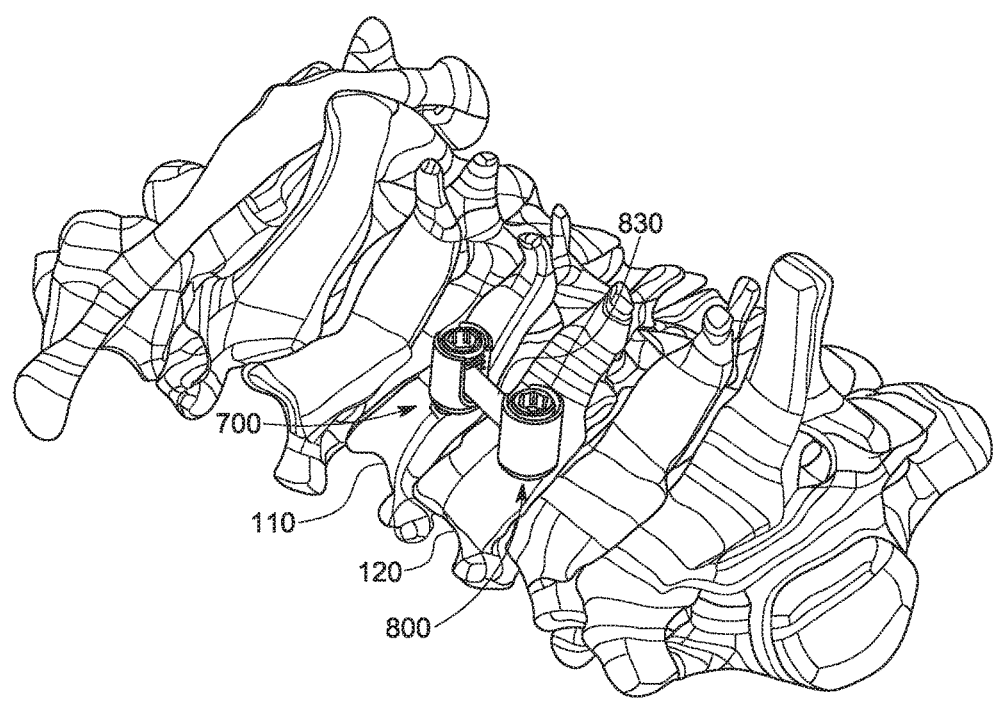
FIG. 17 is an isometric view of a section of cervical vertebrae with two screws and flip-rod installed.

FIG. 17 illustrates an isometric view of a section of cervical vertebrae with an exemplary screw-rod implant installed. In the cervical spine 100, a superior screw assembly 700 is implanted in the superior vertebra 110 and an inferior screw assembly 800 is implanted in the inferior vertebra 120. The screw assemblies are connected by a rod 830 of one of the screw assemblies.

Figure 18:
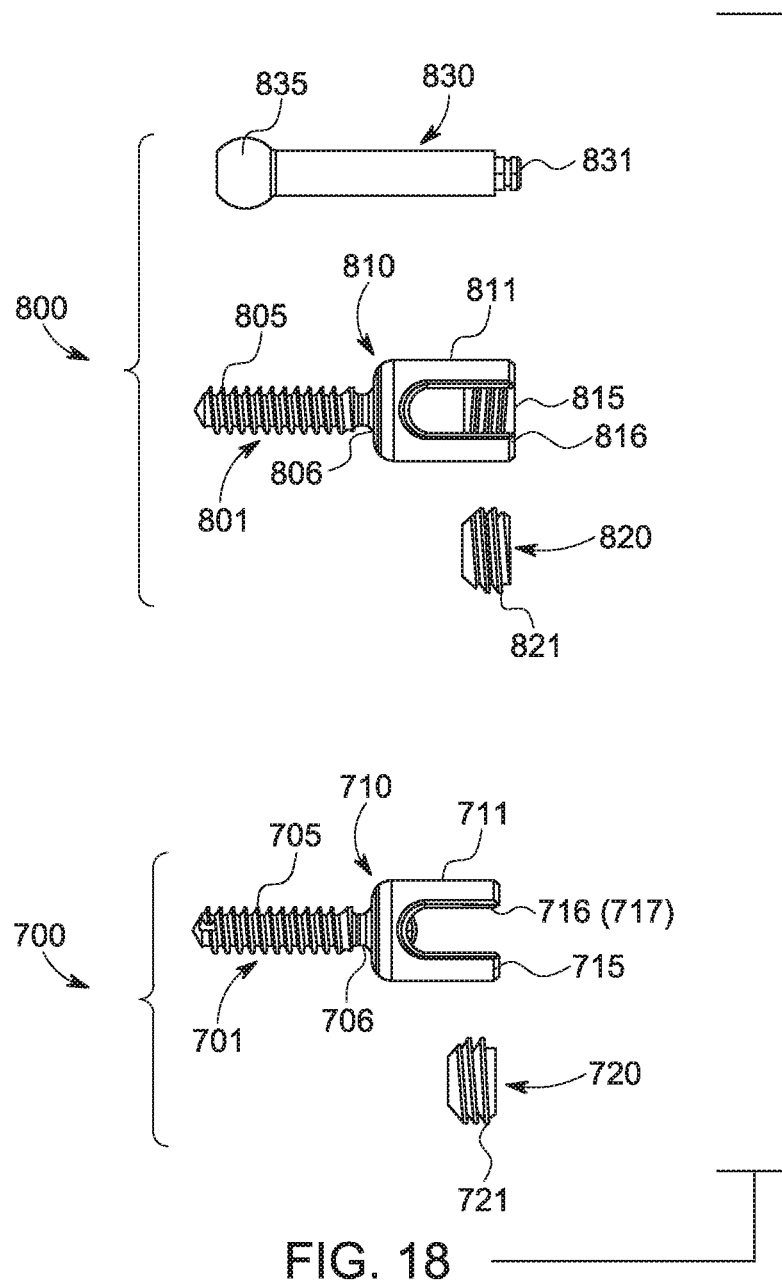
FIG. 18 shows a set of implants used in a spinal fusion system according to an exemplary embodiment of the application.

FIG. 18 shows a set of implants used in a spinal fusion system according to an exemplary embodiment of the application. The superior screw assembly 700 comprises superior screw 710 and locking cap 720. The superior screw 710 in turn comprises shaft part 701 and tulip 711. The shaft part 701 has a threaded shank 705 for engaging the lateral mass and head 706 which mates with the tulip 711 when tightened together. As shown in FIG. 8C, a rounded lower surface 704 of the shaft part 701 engages a rounded upper surface 714 of the tulip 711 when the superior screw 710 is fully tightened. The rounded lower and upper surfaces may alternatively be tapered surfaces. The tulip 711 has slot 716 and another slot 717 arranged to accommodate the rod 830 of the inferior screw assembly 800 when the rod 830 is flipped down into position into the superior screw 710 (see FIG. 14). The tulip 711 further comprises threaded part 715 for engaging with threaded part 721 of locking cap 720. While the threaded part 715 of the tulip 711 is configured to be fitted with the locking cap 720 when fully assembled, the threaded part 715 is also configured to engage with threaded part 516 of superior screw driver 500 to engage the rounded lower surface 704 and the rounded upper surface 714 when superior screw 710 is fully tightened (as described later). The head 706 is further configured to mate with an end 511 of the superior screw driver so that the superior screw 710 can be driven during implantation.

Also shown in FIG. 18, the inferior screw assembly 800 comprises inferior screw 810 and locking cap 820. The inferior screw 810 in turn comprises shaft part 801 and tulip 811. The shaft part 801 has a threaded shank 805 for engaging the lateral mass and head 806 which mates with the tulip 811. In the inferior screw 810, the head 806 of shaft part 801 may also connect to ball 835 of the rod 830 so that the threaded shank 805 can be driven via the rod 830 during installation. The ball 835 is configured to fit in the tulip 811, thus forming a ball-and-socket joint. As shown in FIG. 12B, a rounded lower surface 804 of the shaft part 801 engages a rounded upper surface 814 of the tulip 811 when the inferior screw 810 is fully tightened. The tulip 811 has a slot 816 to accommodate the rod 830 being flipped down into position to connect to the superior screw 710. The tulip 811 further comprises threaded part 815 for engaging with threaded part 821 of locking cap 820. Like the superior screw, while the threaded part 815 of the tulip 811 is configured to be fitted with the locking cap 820 when fully assembled, the threaded part 815 is also configured to engage with threaded part 616 of inferior screw driver 600 to engage the rounded lower surface 804 and the rounded upper surface 814 when inferior screw 810 is fully tightened (as described later). The rod 830 has a tip 831 configured to mate with an end 611 of the inferior screw driver 600 so that the inferior screw 810 can be driven during implantation. This mating configuration may be a snap type (ball latching) quick disconnect employing a spring loaded ball latching mechanism which automatically locks the fittings together when they are pushed together. Other examples include a push-on coupling similar to those typically used for air hoses, for example a quick connect fitting, quick release, or a snap-on connection. In such a fitting, the fitting can be released by pulling back a releasing sleeve (or button) upon which the mating ends quickly disengage from each other.

A cannula which may be used in a surgical procedure for implanting the screw-rod will now be described.

Figure 3:
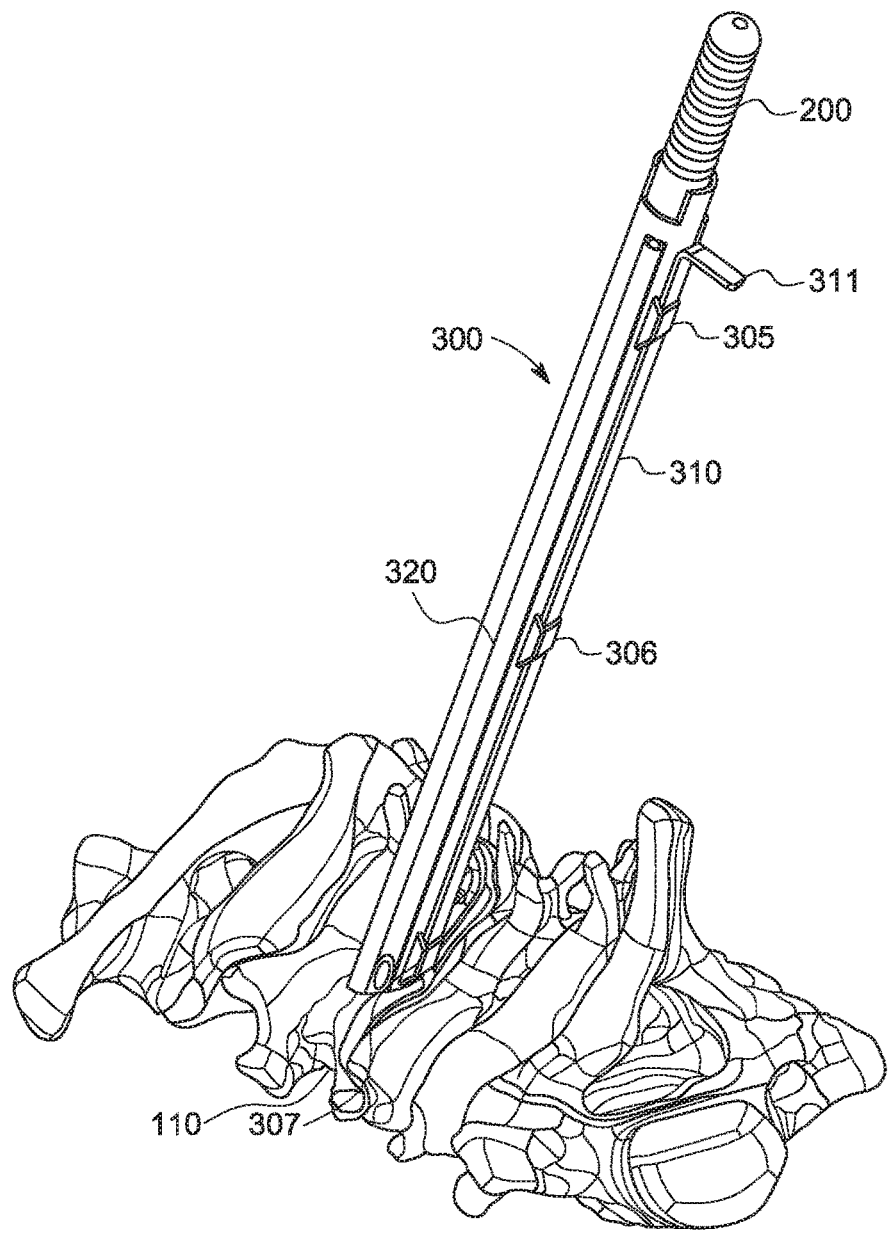
FIG. 3 is an isometric view of a section of cervical vertebrae with an access cannula placed over the dilator.
Figure 5A:
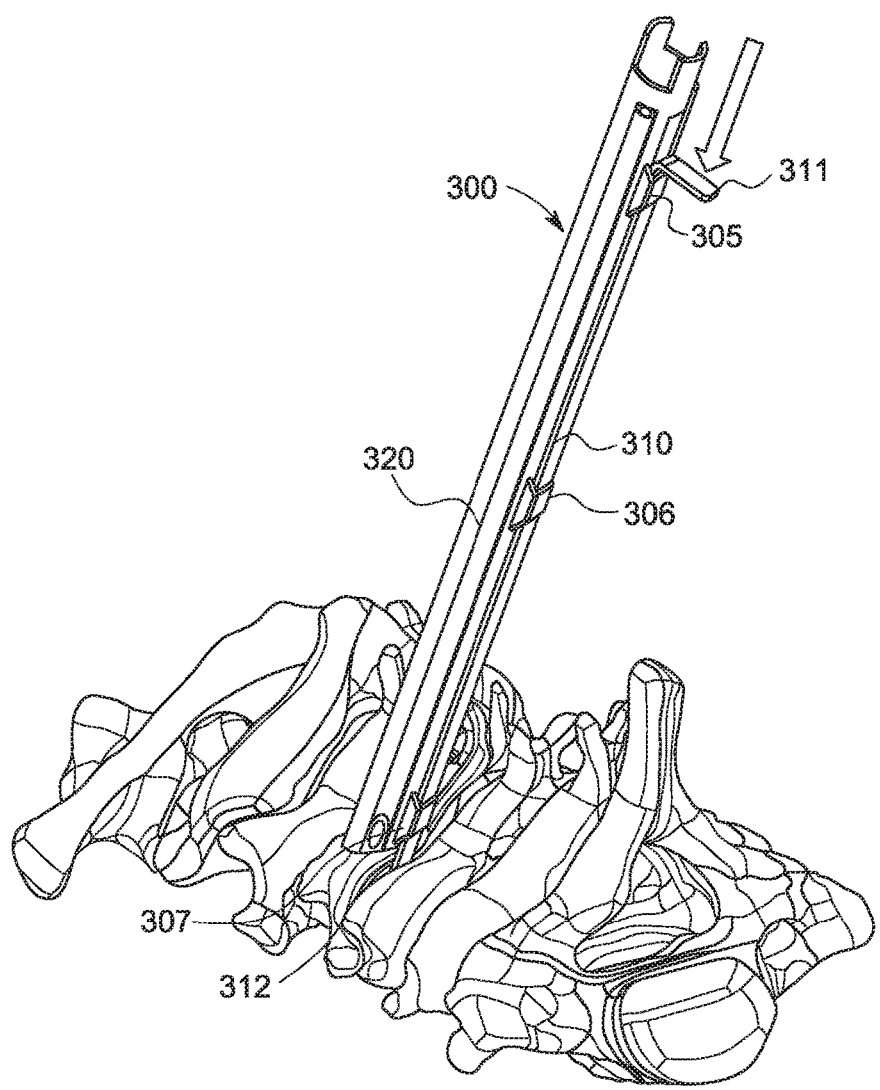
FIG. 5A is an isometric view of a section of cervical vertebrae with a blade of the access cannula being deployed into a facet joint of the vertebrae.
Figure 5B:
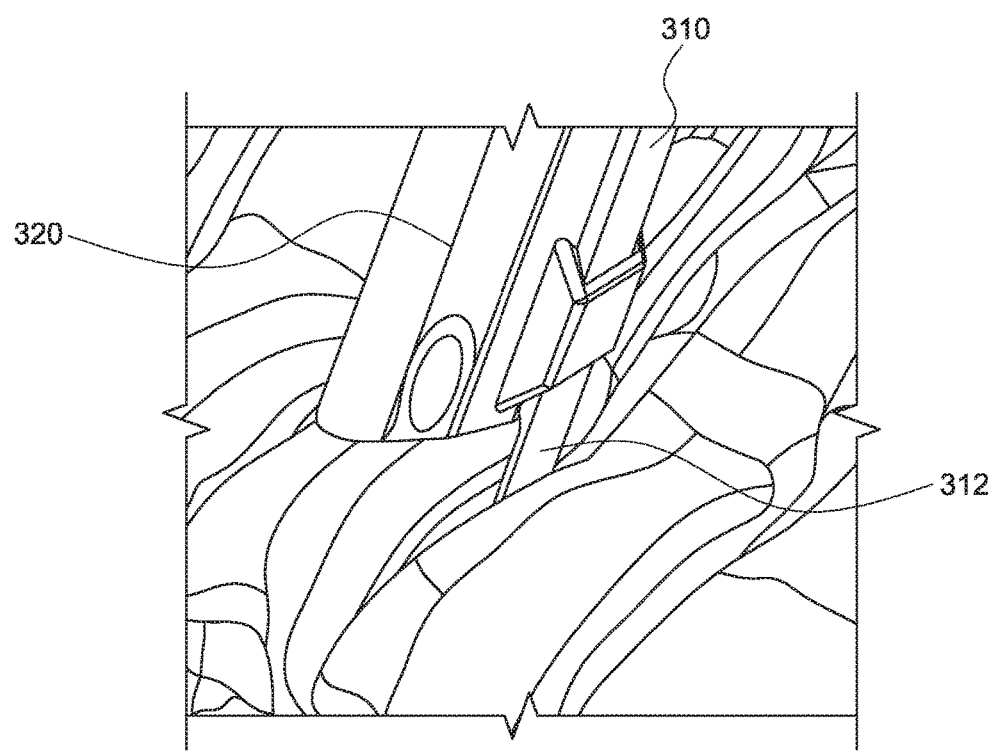
FIG. 5B is a close-up view of the blade in the facet joint.
Figure 6A:
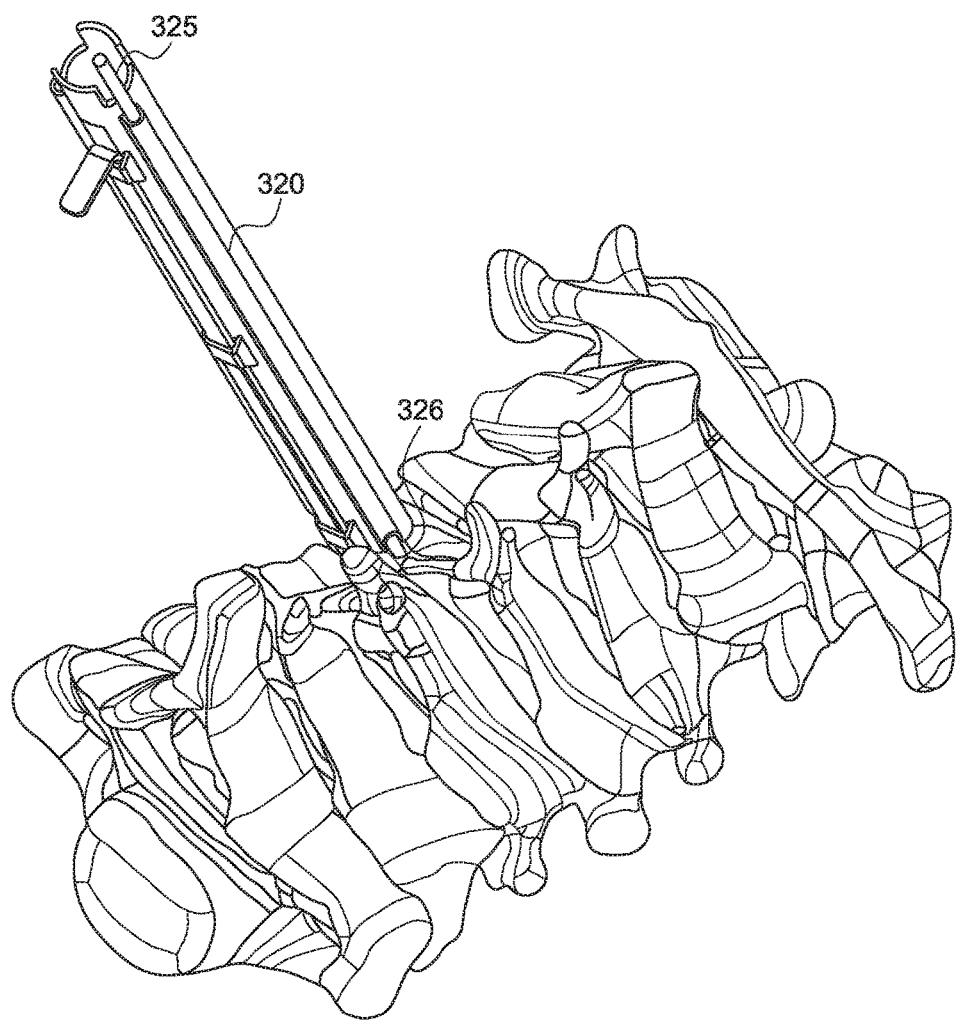
FIG. 6A is an isometric view of a section of cervical vertebrae with a stabilizing wire being inserted into one of the vertebrae.
Figure 6B:
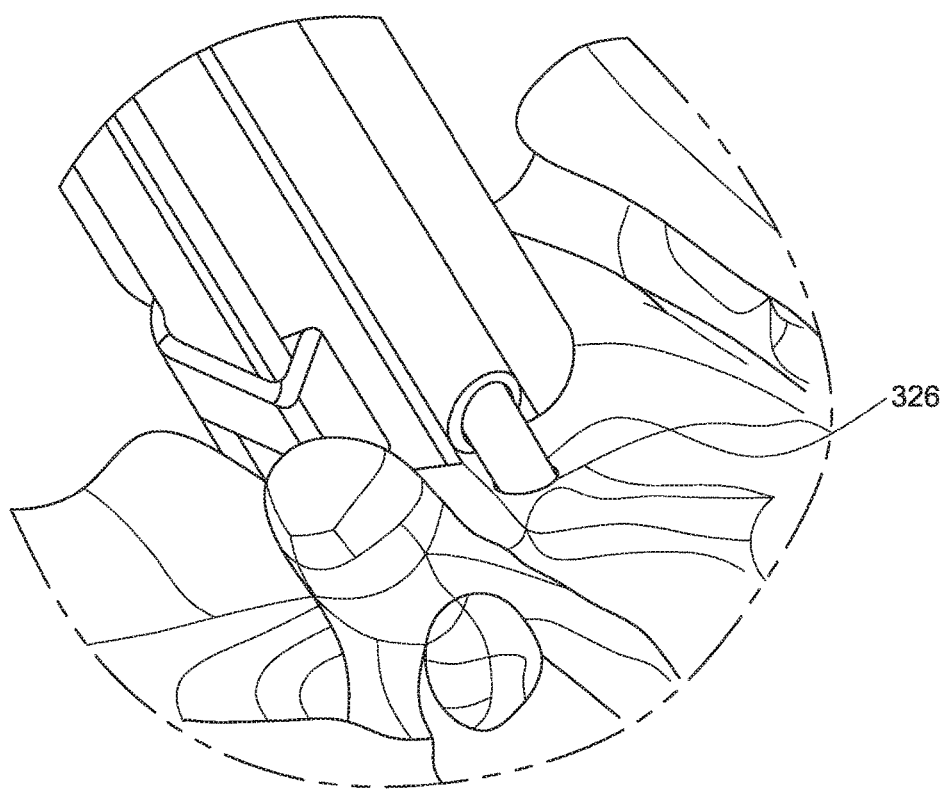
FIG. 6B is a close-up view of the stabilizing wire and vertebra.
Figure 19:
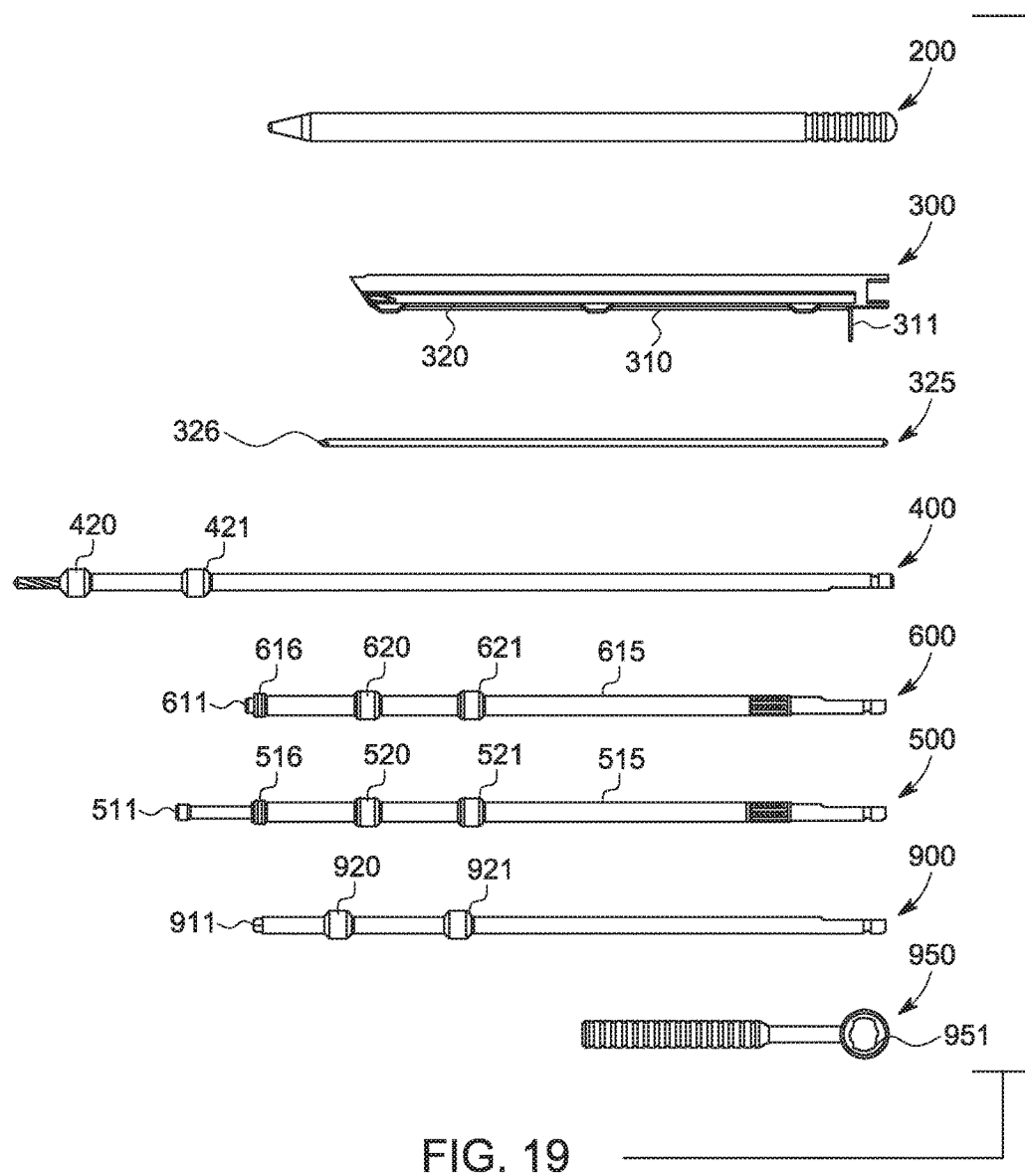
FIG. 19 shows a set of instruments used in a spinal fusion method according to an exemplary embodiment of the application.

The insertion of the screw-rod may be done through an endoscopic access cannula. An exemplary cannula 300 is shown in FIG. 19. As shown in FIG. 3, FIG. 5A, and FIG. 5B, the cannula 300 has a flexible blade 310 with a deployable tip 312 which can be inserted into the facet joint by pressing down on the tab 311 at the top end of the cannula 300. The blade 310 is held in place on the cannula by slots 305, 306, and 307. The cannula 300 also has a parallel channel 320 through which a small stabilizing pin 325 can be placed into the lateral mass to help stabilize the final position of the cannula 300 prior to drilling. The stabilizing pin 325 may be a K-wire. As shown in FIG. 6A and FIG. 6B, once the cannula is in the appropriate position, a tip 326 of the stabilizing pin 325 is inserted into the lateral mass and the cannula 300 can thus be anchored in place. The blade 310 has a substantially planar shape, and the channel 320 for inserting the stabilizing pin 325 is offset from the line formed by the edge of the tip 312. The positioning of the stabilizing pin 325 being offset from the line of the blade 310 provides the cannula with better leverage for resisting lateral forces. This allows the cannula 300 to be fixed stably in place. It should be noted that the accompanying drawings depict the stabilizing pin 325 being inserted through channel 320 on one side of the cannula 300. However, stabilizing pin 325 could be inserted through another channel disposed on the other side of the cannula. The cannula 300 may be provided with two channels on both sides or with only one channel on one side. An advantage of a dual channel arrangement is that the cannula can be used equally well on left or right sides of a vertebra. Furthermore, a dual channel arrangement provides the ability to deploy two stabilizing pins simultaneously, which may provide further stability, if needed.

The cannula may be configured to allow the insertion and manipulation of an endoscope. Accordingly, the cannula may be configured to mate with an adaptor at the top of the cannula that prevents endoscopic fluid from escaping. Such an adapter may be further configured with inlet and outlet channels to provide inflow and outflow of irrigation fluid.

The process of implanting the screw-rod will now be described in further detail with reference to an exemplary surgical procedure.

Figure 20:
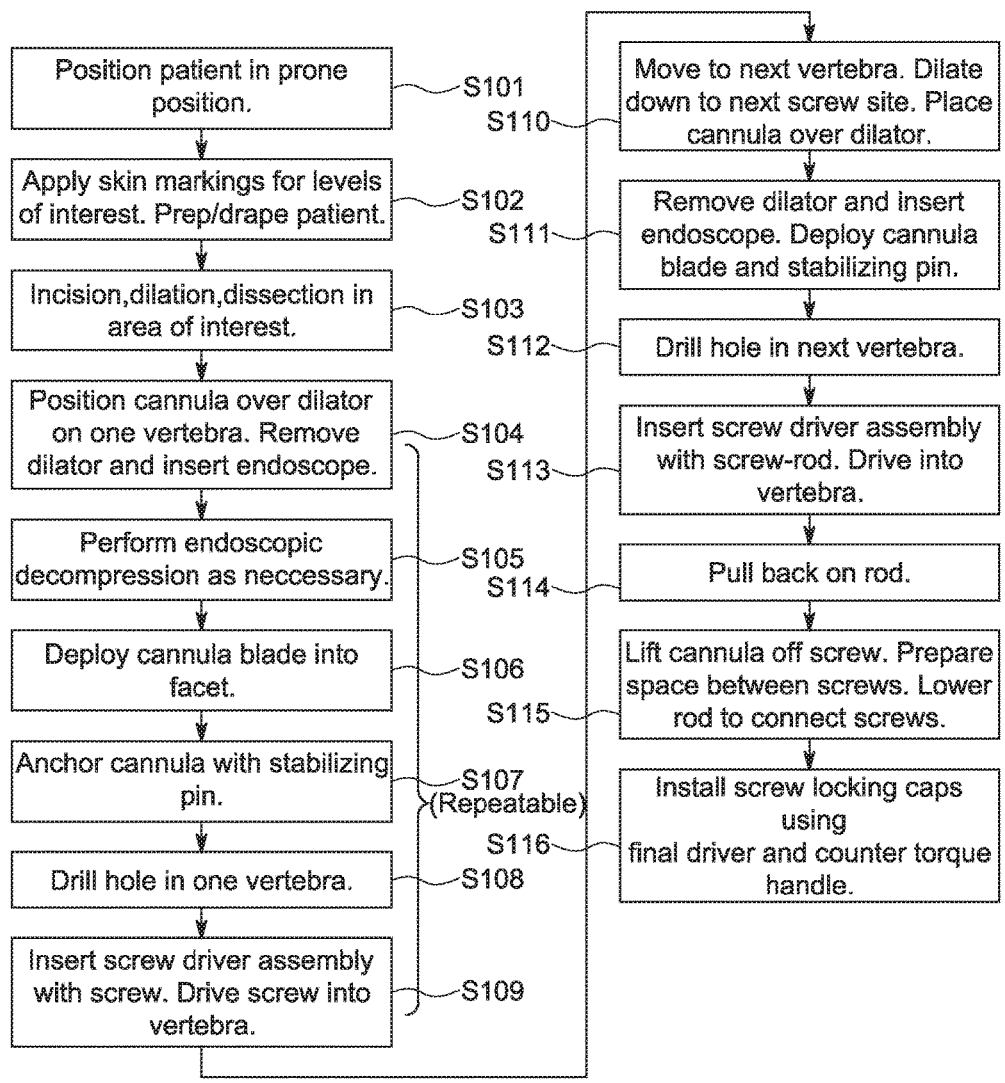
FIG. 20 is a flow chart representing a procedure for spinal fusion according to an exemplary embodiment of the application.

An exemplary surgical procedure is outlined by the flowchart of FIG. 20. In a first step S101, a patient is placed in the prone position using, for example, the Mayfield Head Holder.

In a second step S102, Anteroposterior (AP) and Lateral fluoroscopy imaging are used to define levels of interest and make skin markings. The patient is then prepared for surgery and draped.

Figure 2:
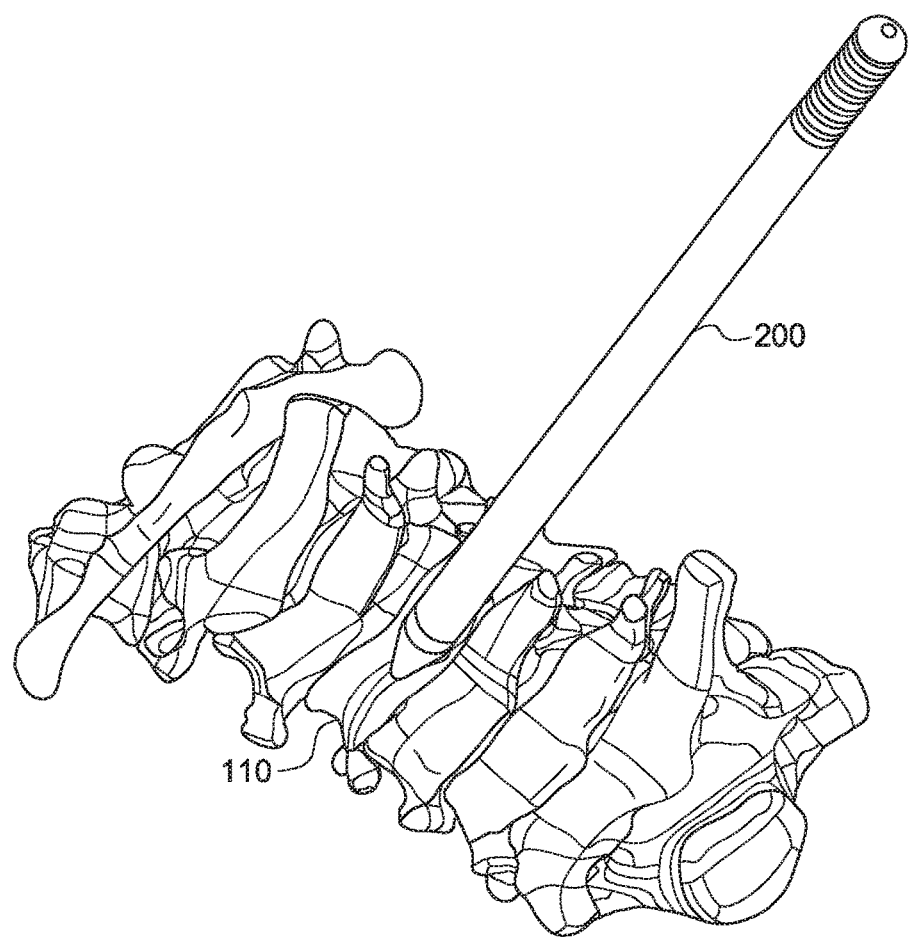
FIG. 2 is an isometric view of a section of cervical vertebrae with a dilator.

In a third step S103, a 7 mm incision is made on one side of the posterior cervical spine. An inter-muscular approach is performed using a 2 hole obturator, also known as a "dilator", which is depicted schematically in the accompanying drawings by dilator 200, for example in FIG. 2. A process of wanding can be used to elevate muscle and capsular tissue from the lateral mass, thus opening a cavity. The dilator 200 can be used to bluntly dissect the muscle and detect the contours of bony elements. The facet of interest is outlined superiorly and inferiorly. The dilator 200 is used to dilate down to the superior lateral mass screw placement site on the superior vertebra 110, as shown in FIG. 2.

Figure 4:
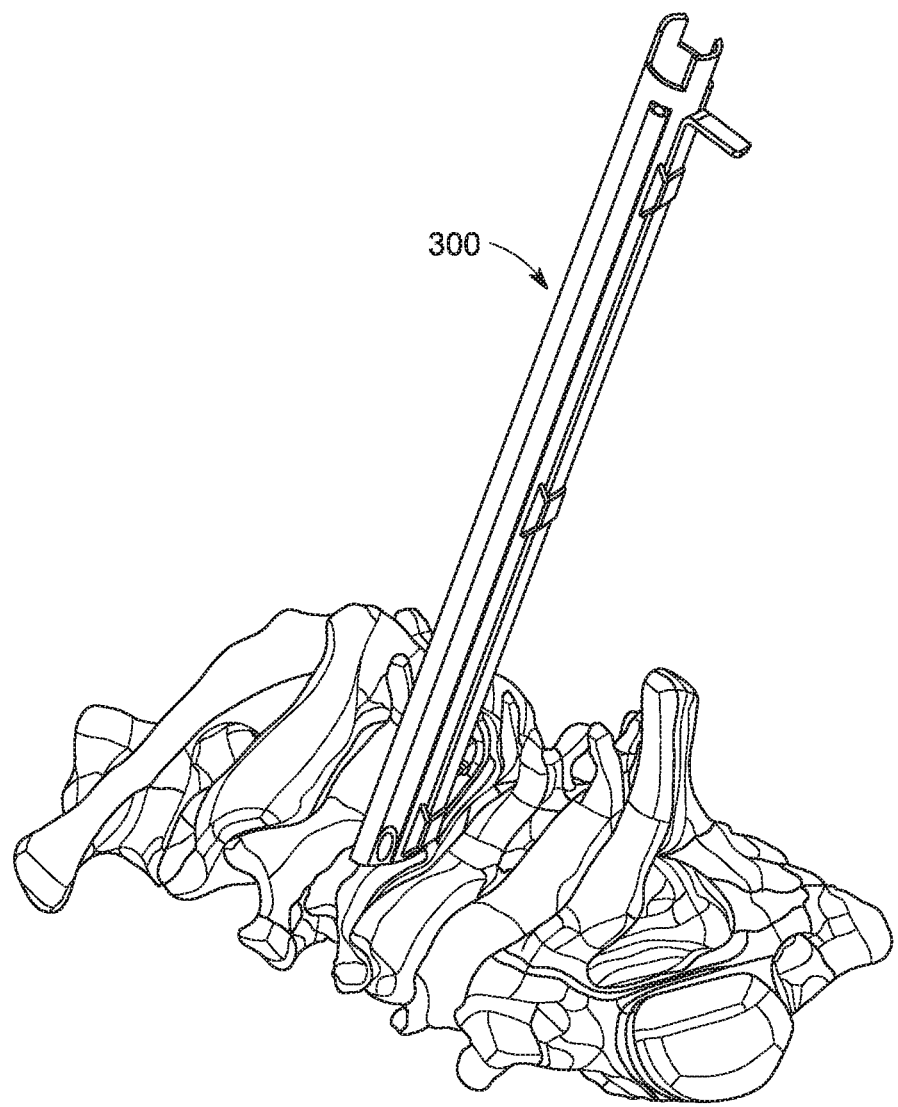
FIG. 4 is an isometric view of a section of cervical vertebrae with an access cannula in which the dilator has been removed.

In a fourth step S104, as shown in FIG. 3, the cannula 300 is positioned over the dilator 200. The dilator is then removed, as shown in FIG. 4. At this point, an endoscope is inserted in the cannula and the lateral mass screw placement site is cleaned using an electro-cautery to remove tissue covering the bone.

At this stage, in an optional fifth step S105, endoscopic decompression of the spine is performed as necessary. Spinal decompression therapy is known in the art and will not be described here in detail. However, it should be noted that performing decompression of the spine through an endoscope has recently attracted attention as a minimally invasive approach. In such an approach, a surgeon may move bone spurs off of the nerves (spinal cord) using various instruments with the aid of an endoscope inserted through a cannula. After the bony elements and features that press on nerves are repositioned, a spinal fusion system as discussed in this application may be implanted to fix the spine in a position to prevent future compression of nerves.

However, the decompression step discussed above is optional. For example, one can use the spinal fusion system of this application in the case of arthritic neck pain, but no decompression is required to relieve pain.

In a sixth step S106, as shown in FIG. 5A and FIG. 5B, with assistance from the endoscope still in the cannula 300, the cannula is appropriately positioned and the blade 310 of the cannula 300 is deployed by advancing the tip 312 into the facet joint space. The flexibility of the blade 310 allows some angulation of the cannula 300 without losing position on the lateral mass.

In a seventh step S107, as shown in FIG. 6A and FIG. 6B, stabilizing pin 325 is inserted into the lateral mass to anchor the cannula in an appropriate position in preparation for drilling. The use of stabilizing pin 325 may be optional, but provides additional stability when used. Upon fixing the cannula in position, the endoscope can be removed.

Figure 7A:
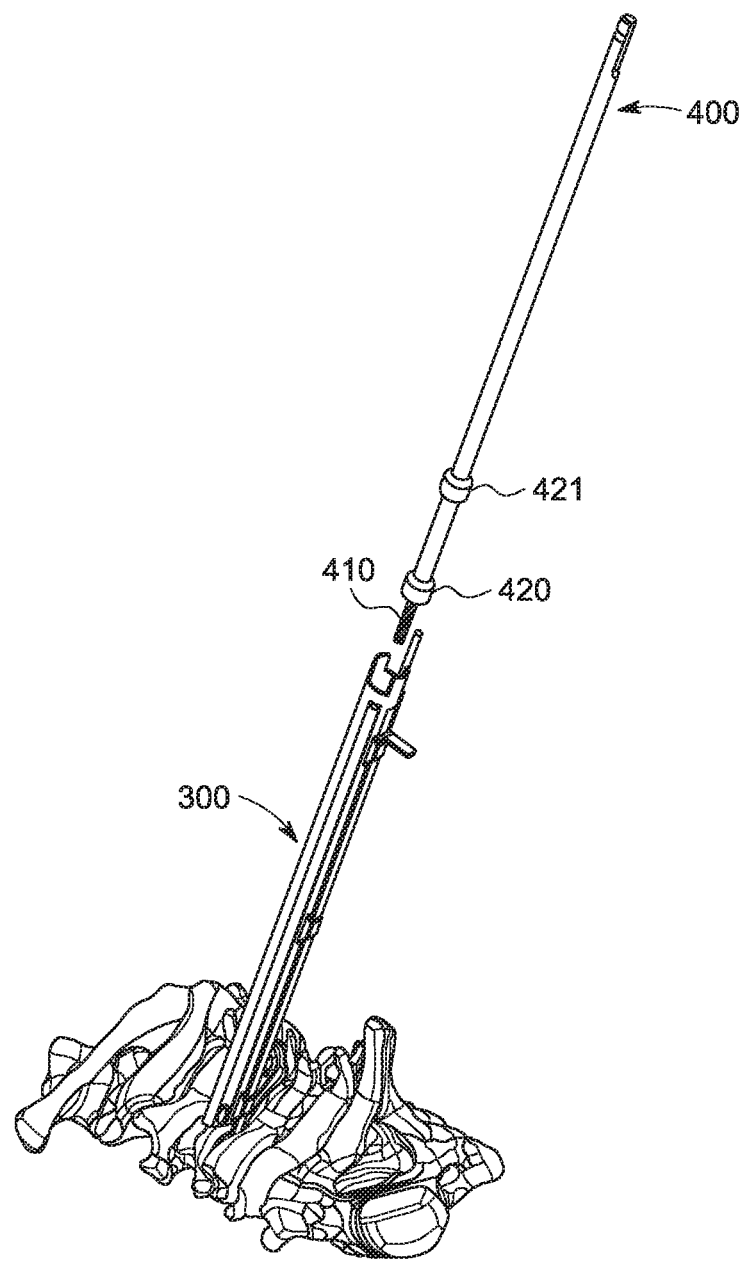
FIG. 7A is an isometric view of a section of cervical vertebrae with a drill being inserted into the access cannula.
Figure 7B:
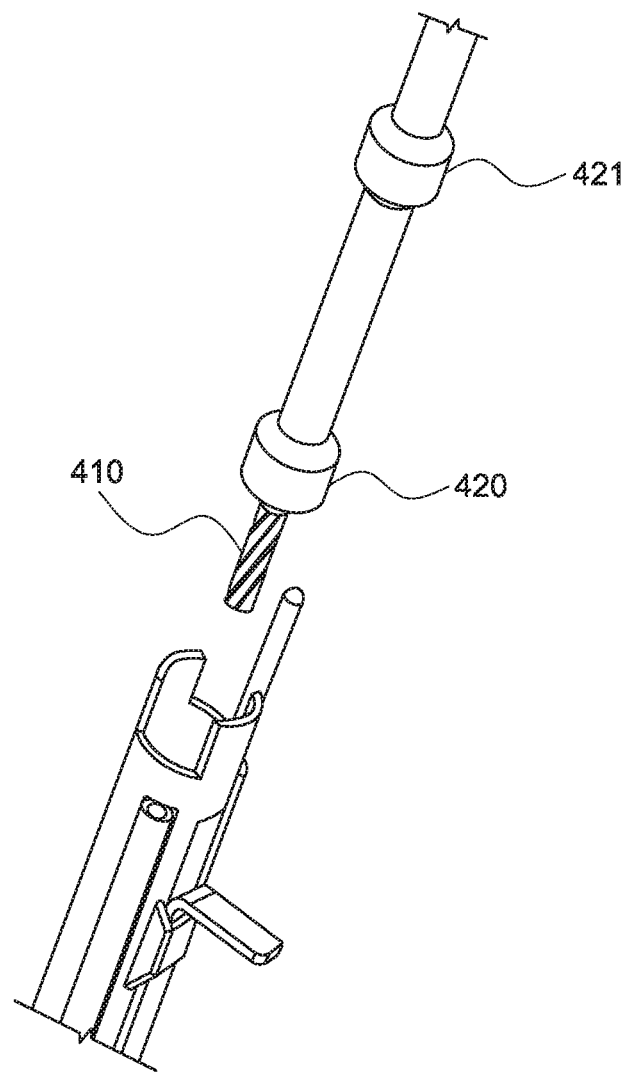
FIG. 7B is a close-up view of the drill.

In an eighth step S108, as shown in FIG. 7A and FIG. 7B, after the endoscope is removed, a drill with a shaft slightly smaller in diameter than that of the cannula 300 is placed down the fixed cannula 300. An exemplary drill 400 has bushings 420 and 421 which closely match the inner diameter of the cannula 300 and which keep the drill 400 centralized in the cannula 300. The drill 400 has a tip 410 by which a screw hole is drilled in the lateral mass.

Figure 8A:
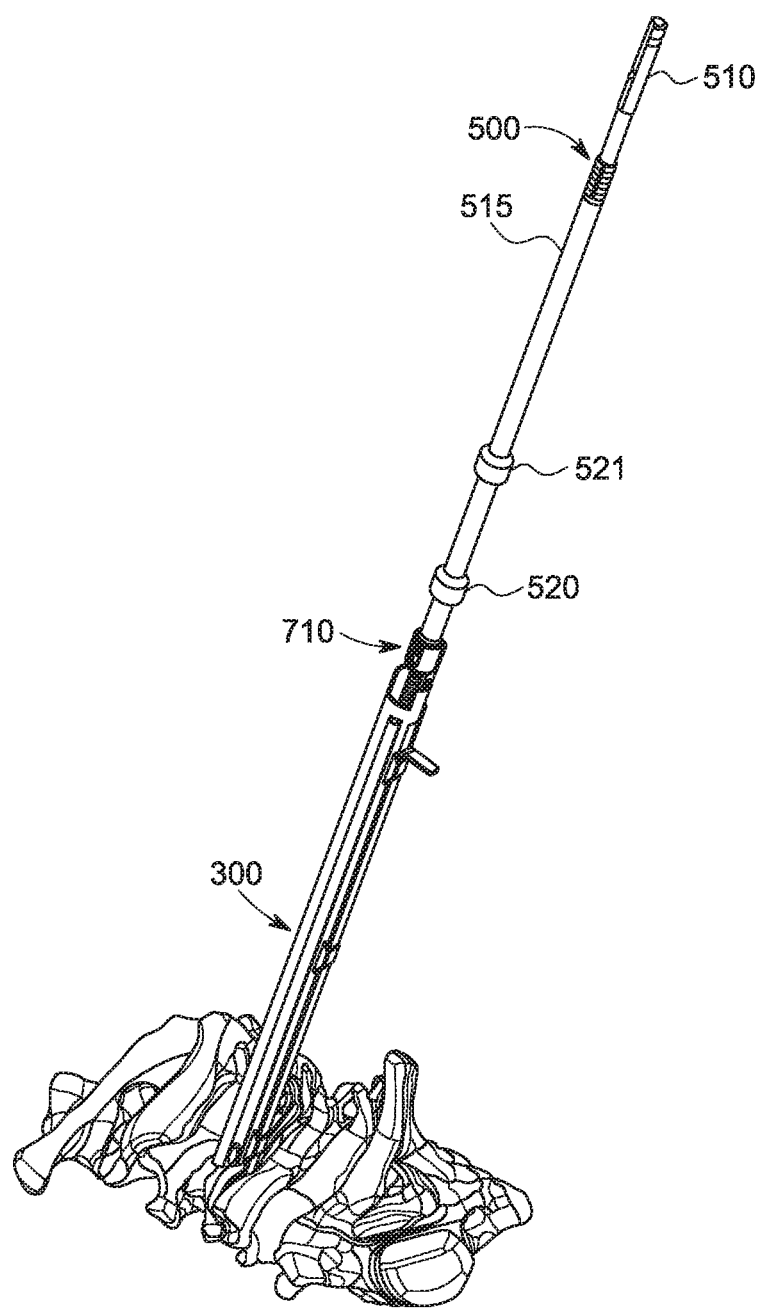
FIG. 8A is an isometric view of a section of cervical vertebrae with a screw driver assembly being inserted into the access cannula.
Figure 8B:
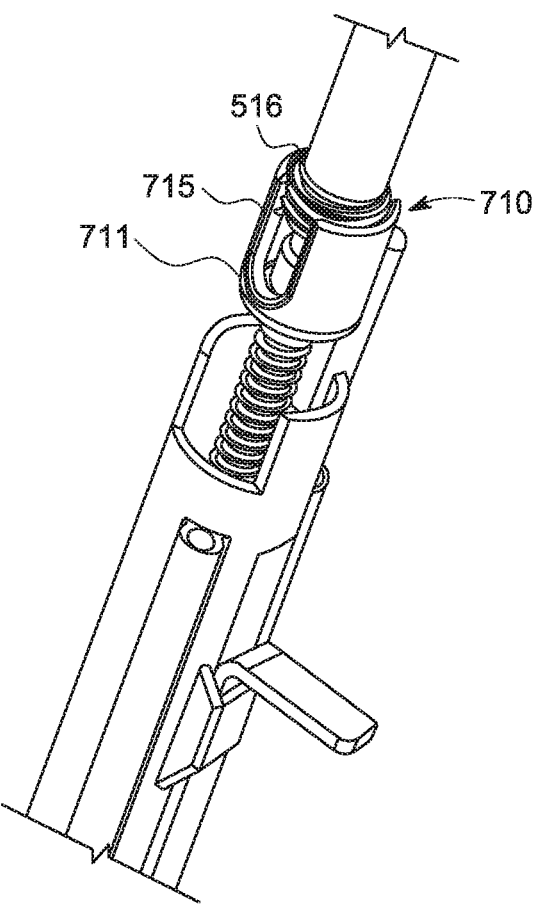
FIG. 8B is a close up of the screw driver assembly.
Figure 8C:
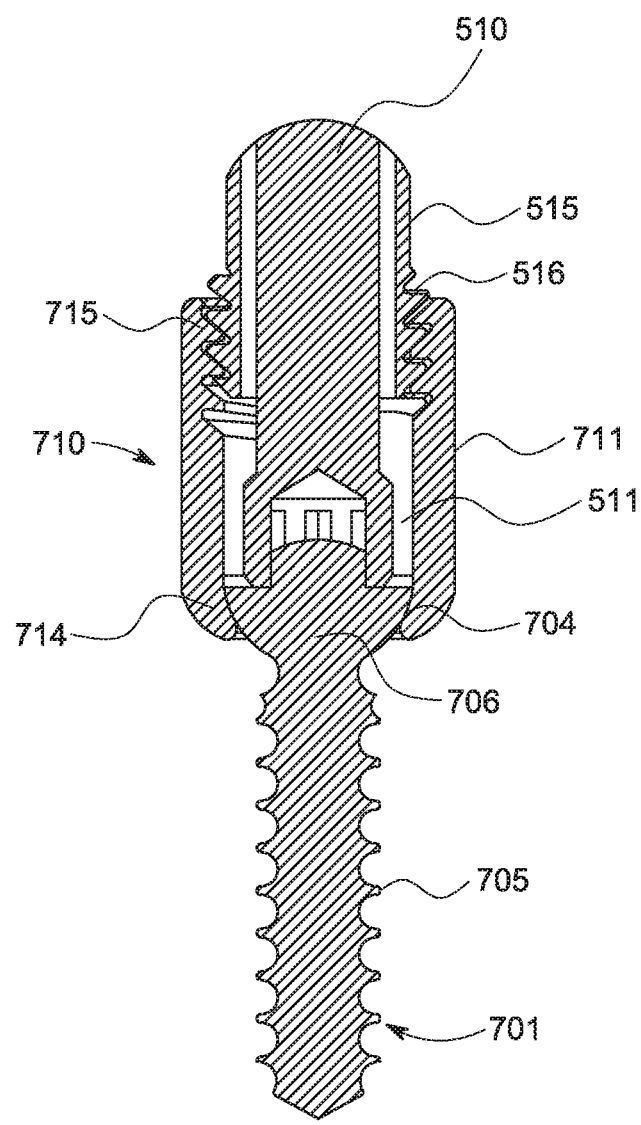
FIG. 8C is a cross section of the screw driver assembly.

In a ninth step S109, as shown in FIG. 8A and FIG. 8B, superior screw 710 is attached to superior screw driver 500 and inserted in the cannula 300. The superior screw driver 500 comprises an inner shaft 510 and an outer sleeve 515 which may rotate independently of one another. On the outer sleeve 515 are bushings 520 and 521, which keep the screw driver 500 centralized in the cannula 300. The outer sleeve 515 also has a threaded part 516 which engages the threaded part 715 of the tulip 711 of the superior screw 710. An end 511 of the inner shaft 510 engages the head 706 of the shaft part 701 of the superior screw 710. Since the superior screw assembly 700 does not comprise the rod 830, the end 511 of the inner shaft 510 protrudes from the outer sleeve 515 so that the screw can be driven.

When superior screw 710 is being driven into the lateral mass, care is taken to align slots 716 and 717 with the planned position of the inferior screw site such that the rod 830 may fit in the slots when connected. The tulip 711 may have etch markings that match up with etch markings on the inside of the cannula 300 to assist in positioning.

FIG. 8C shows a mechanism by which the superior screw 710 is tightened when being driven into place in the lateral mass. The tulip 711 of the superior screw 710 is coupled to the outer sleeve 515 of the superior screw driver 500 by threaded parts 715 and 516. When this threaded coupling is only partially engaged, however, the tulip 711 and the head 706 of the shaft part 701 are not pressed into contact with each other. In this state, the shaft part 701 and inner shaft 510 may float within the tulip 711 and outer sleeve 515, therefore allowing for slight adjustments in positioning the screw into the screw hole. Then, together with driving the superior screw 710 to advance the threaded shank 705 into the screw hole in the lateral mass, the coupling between threaded parts 715 and 516 is also tightened by rotating the outer shaft 515. This causes the rounded part 704 of the head 706 to be brought into contact with the rounded part 714 of the tulip. When the superior screw 710 is fully tightened, the rounded part 704 and rounded part 714 are in press contact and locked together.

Figure 9A:
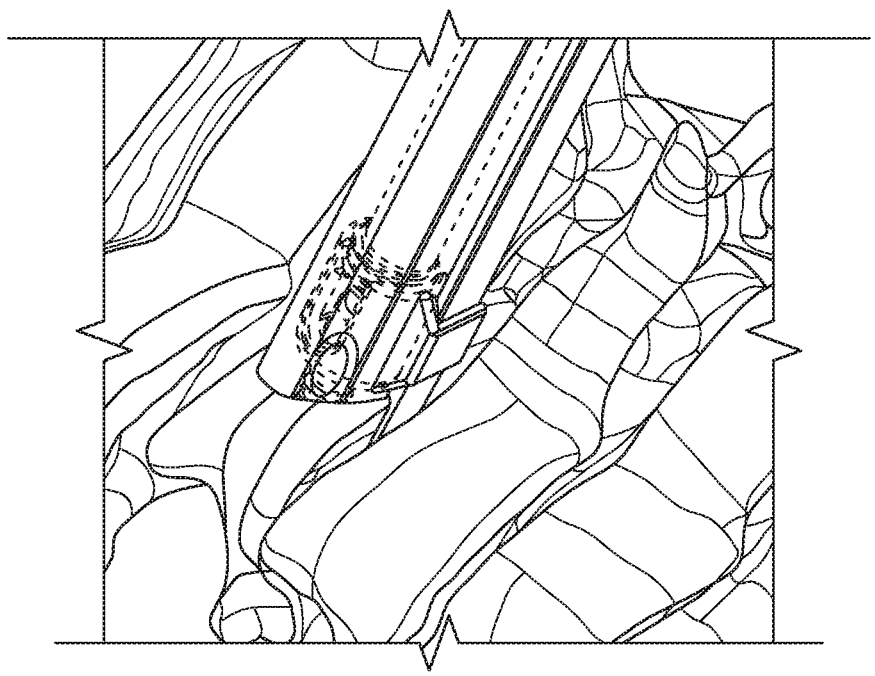
FIGS. 9A-9C illustrate a screw being driven into place in a vertebra and the screwdriver being removed.
Figure 9B:
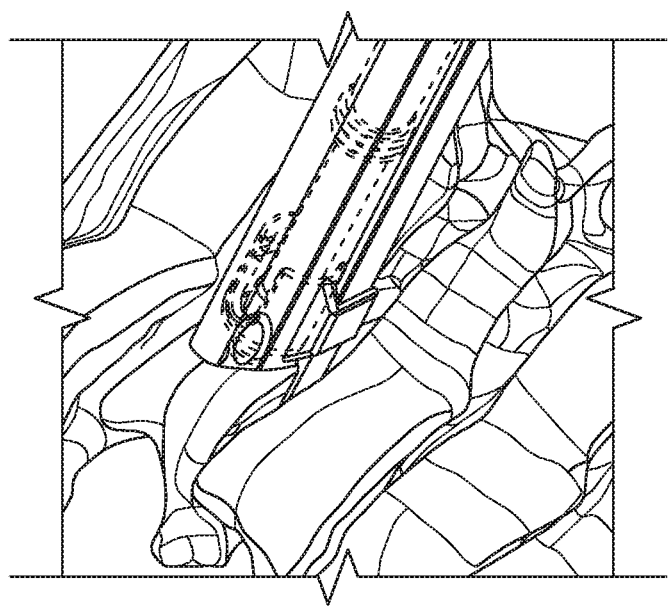
Figure 9C:
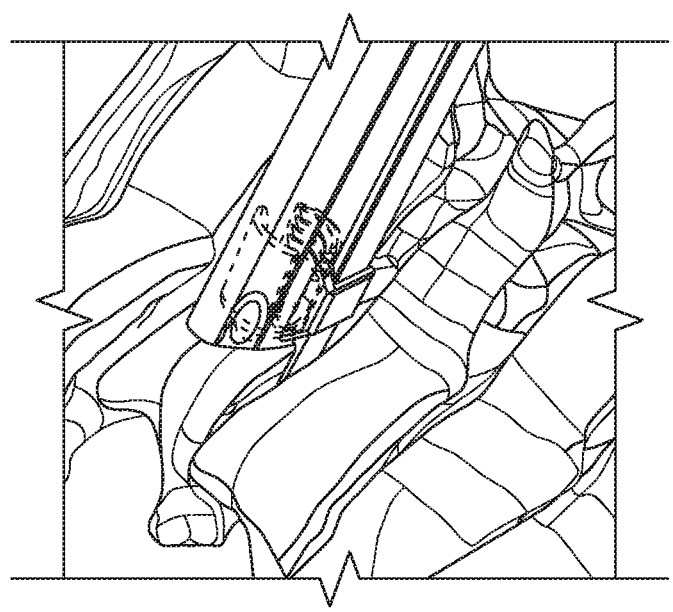

As shown in FIG. 9A, the superior screw 710 is driven into place as described above. Then, as shown in FIG. 9B, the outer sleeve 515 is unthreaded from the tulip 711. Finally, as shown in FIG. 9C, the superior screw driver 500 is retracted and removed from the cannula 300.

Figure 10:
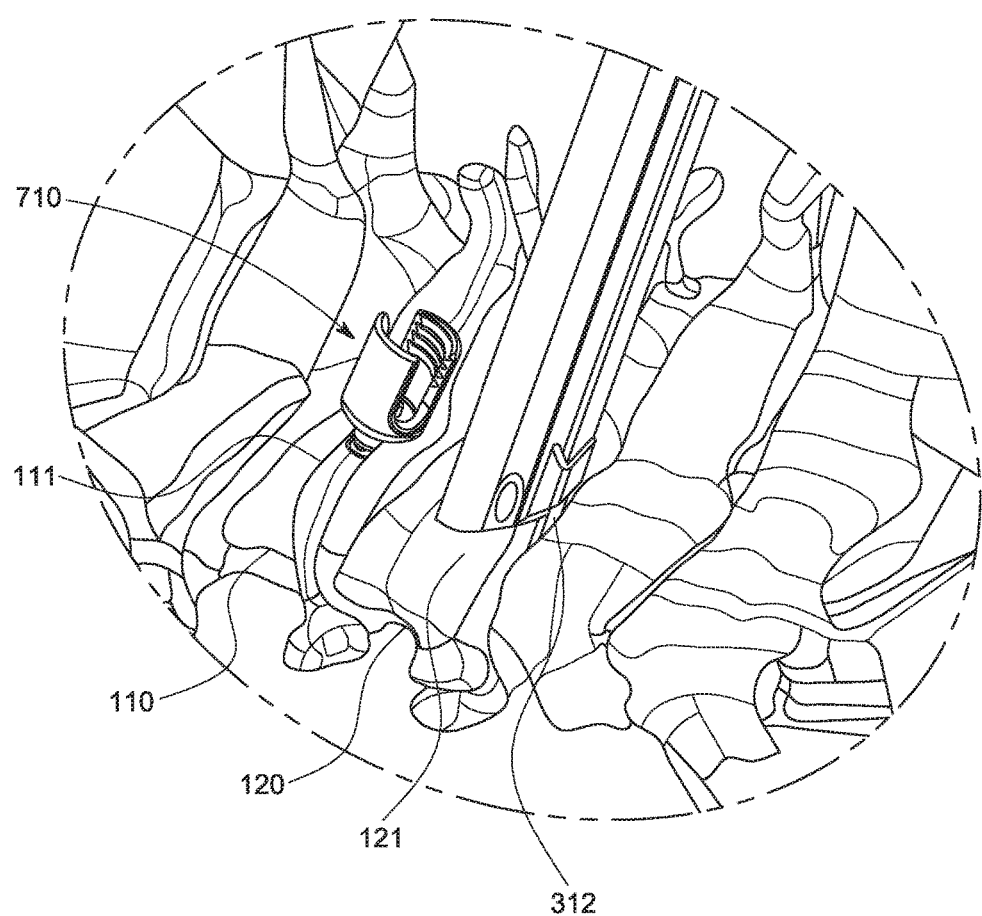
FIG. 10 is a close-up isometric view of a section of cervical vertebrae with the access cannula being repositioned to another site.

Next, beginning with a tenth step S110, the above procedure is substantially repeated for the adjacent vertebra. For example, the dilator 200 is used to dilate down to the next screw site on the inferior vertebra 120. The cannula 300 is then placed over the dilator 200 and the dilator 200 is removed. Next, in an eleventh step S111, the endoscope is inserted to assist in precise positioning and, as shown in FIG. 10, the tip 312 of the blade 310 is advanced into the next facet joint and the cannula 300 is anchored by additionally deploying the stabilizing pin 325. The endoscope is now removed in preparation for drilling.

Figure 11:
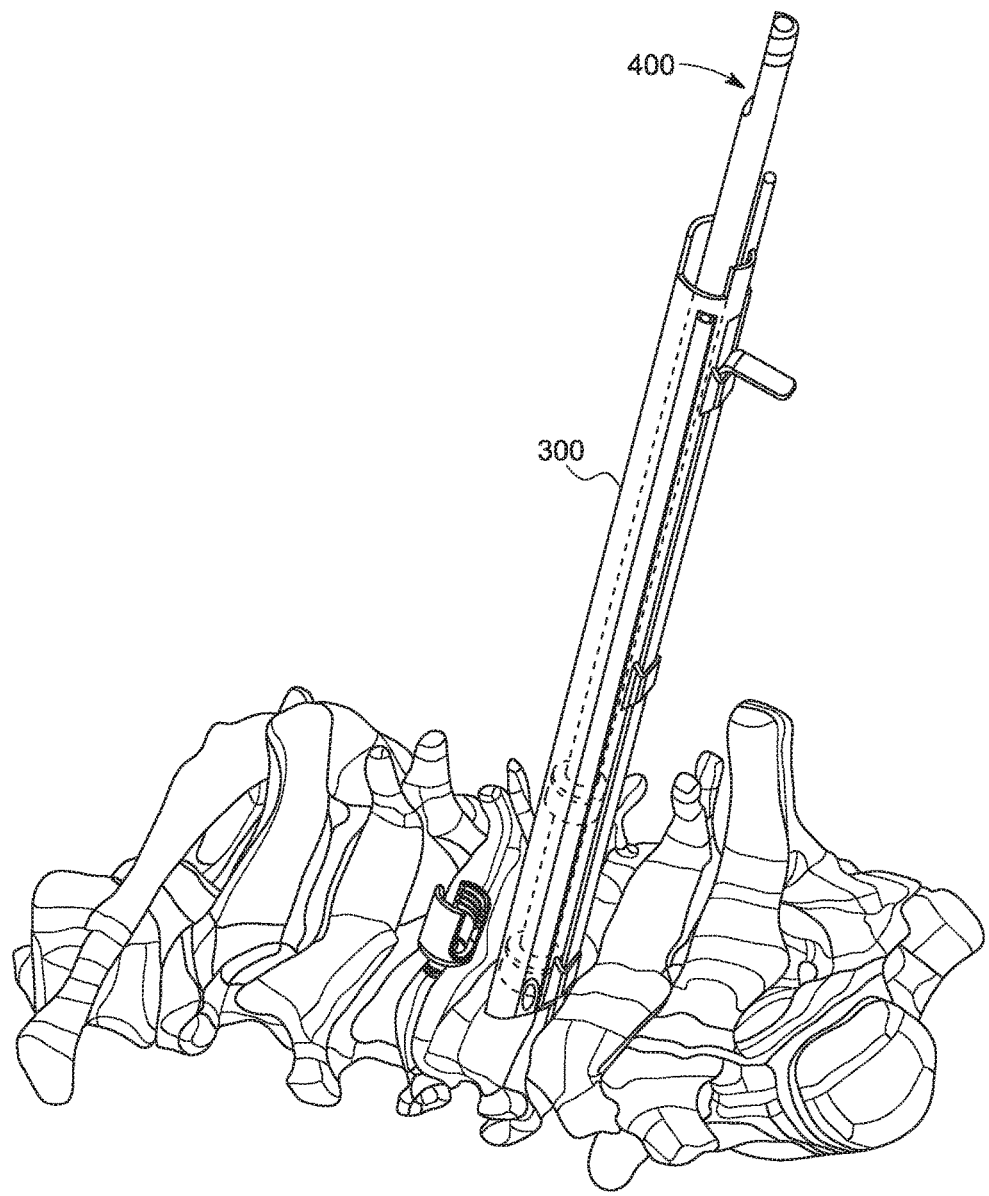
FIG. 11 is an isometric view of a section of cervical vertebrae with a drill being inserted into the access cannula.

In a twelfth step S112, as shown in FIG. 11, the drill 400 is placed in the cannula 300, and drilling of an inferior hole is performed.

Figure 12A:
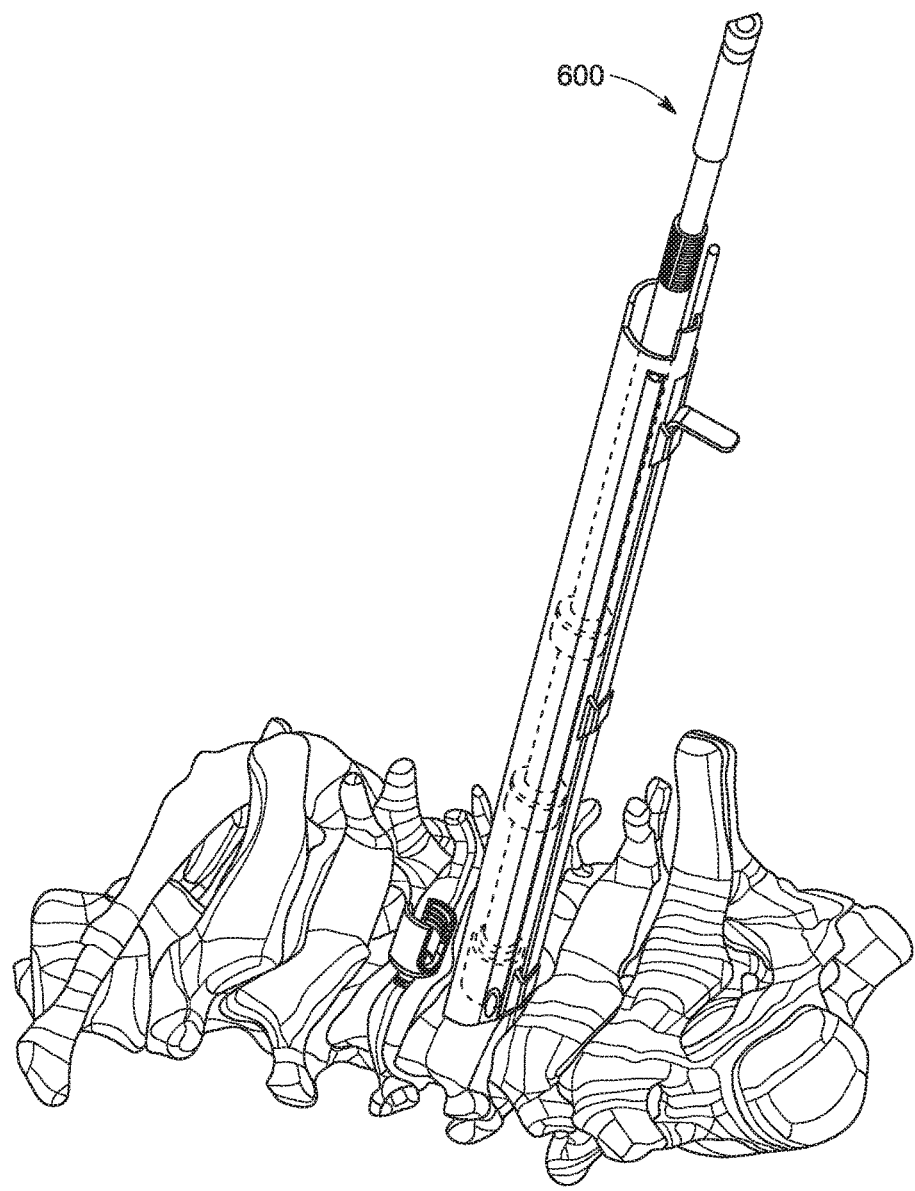
FIG. 12A is an isometric view of a section of cervical vertebrae with a screw and rod assembly being inserted into the access cannula.
Figure 12B:
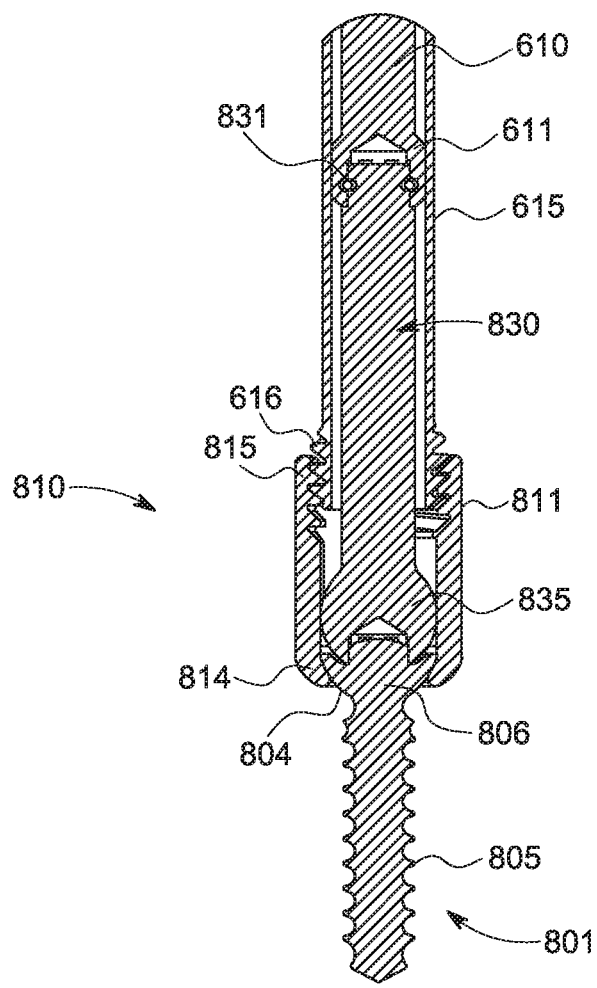
FIG. 12B is a cross section of the screw and rod assembly attached to a screw driver assembly.

In a thirteenth step S113, as shown in FIG. 12A, a screw-rod is placed. The screw-rod may be exemplified by inferior screw 810, wherein rod 830 is temporarily attached to the head 806 of the shaft part 801 of the inferior screw 810 for installation. As shown in FIG. 12A and FIG. 12B, inferior screw driver 600 is attached to the tip 831 of the rod 830. The inferior screw driver 600 comprises an outer sleeve 615 and an inner shaft 610, independently rotatable, wherein inner shaft 610 connects to the tip 831 of the rod 830 by an end 611 of the inner shaft 610. On the outer sleeve 615 are bushings 620 and 621, which keep the screw driver 600 centralized in the cannula 300. The outer sleeve 615 also has a threaded part 616 which engages the threaded part 815 of the tulip 811 of the inferior screw 810. During installation, the end 611 of the inner shaft 615 does not protrude from the outer sleeve 515 when driving the screw-rod.

When the inferior screw 810 is being driven into the lateral mass, slot 816 of the tulip 811 is aligned with the slots 716 and 717 of the superior screw 710. Like the superior screw, the tulip 811 may have etch markings that match up with etch markings on the inside of the cannula 300 to assist in positioning.

FIG. 12B shows a mechanism by which the inferior screw 810 is tightened via the rod 830 when being driven into place in the lateral mass. Like the superior screw, the tulip 811 of the inferior screw 810 is coupled to the outer sleeve 615 of the inferior screw driver 600 by threaded parts 815 and 616. When this threaded coupling is only partially engaged, however, the tulip 811 and the head 806 of the shaft part 801 are not pressed into contact with each other. In this state, the shaft part 801, the rod 830, and the inner shaft 610 may slide within the tulip 811 and outer sleeve 615, therefore allowing for slight adjustments in positioning the screw into the screw hole. Then, together with driving the inferior screw 810 to advance the threaded shank 805 into the screw hole in the lateral mass, the coupling between threaded parts 815 and 616 is also tightened by rotating the outer sleeve 615 and the rounded part 804 of the head 806 contacts the rounded part 814 of the tulip 811. When the inferior screw 810 is fully tightened, the rounded part 804 and rounded part 814 are in press contact and locked together.

Figure 13:
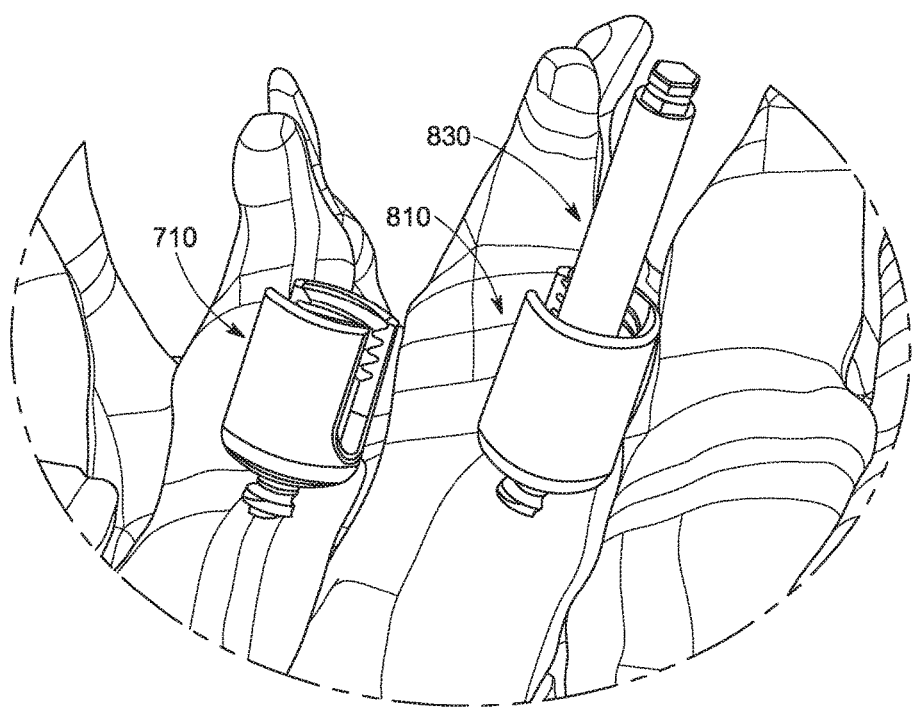
FIG. 13 is a close-up view of a section of cervical vertebrae with two screws installed.

In a fourteenth step S114, the surgeon pulls back on the rod 830 with the inferior screw driver 600 to disconnect the temporary coupling of the ball 835 and the head 806 of inferior screw 810. The tulip 811 may have stop features (not shown) protruding from the inner circumferential surface of the tulip 811 which prevent the rod 830 from being fully removed from the tulip 811. The stop features could be a narrowing of the tulip inner diameter provided such that the diameter of the narrowing is slightly smaller than the diameter of the ball. Alternatively, without using such stop features, the rod 830 may be pulled back until the ball 835 contacts an end of the outer sleeve 615 of the inferior screw driver 600 to disconnect the coupling of the rod 830 and inner shaft 610, after which the inferior screw driver can be unthreaded and retracted. Furthermore, the attachment of the rod 830 to inner shaft 610 of inferior screw driver 610 may be actuatable such that the surgeon can actively control the coupling. For example, a button (not shown) may be provided on the inferior screw driver 600 that, when pressed, causes the tip 831 to disengage from the end 611. This attachment mechanism may be a snap type latching connection. When the ball 835 is disengaged from the head 806 and then disengaged from the inner shaft 610, the ball can rotate within the tulip 811, thus forming a ball-and-socket joint. At the completion of this step, the superior screw 710 and inferior screw 810 with rotatable rod 835 are installed in adjacent lateral masses, as shown in FIG. 13. Although not shown in FIG. 13, the cannula 300 still covers the inferior screw 710 and rod 830.

Figure 14:
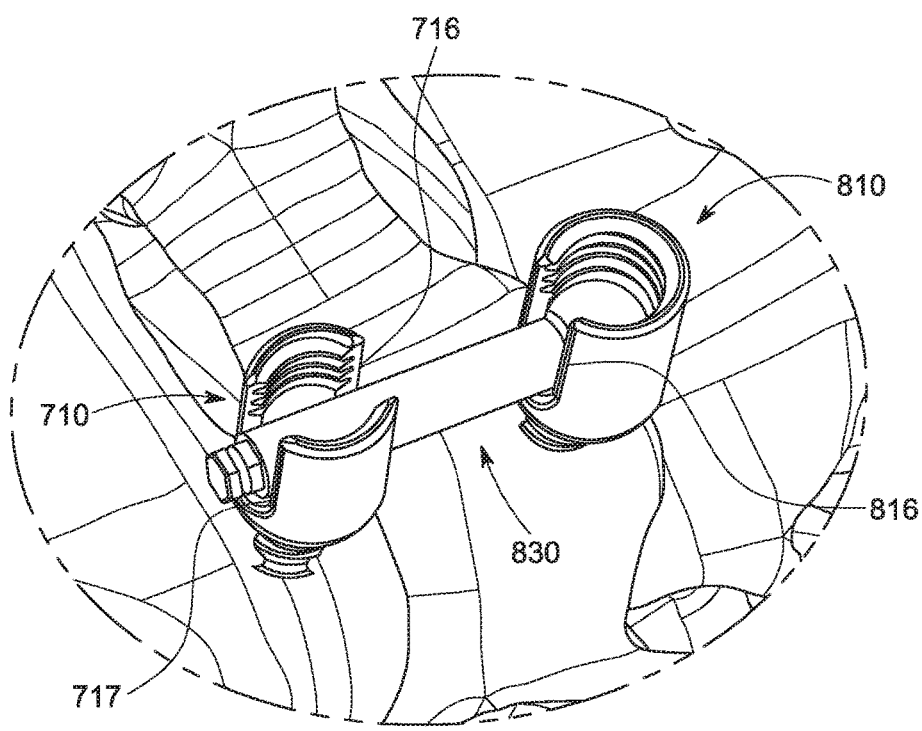
FIG. 14 is a close-up view of a section of cervical vertebrae with two screws and flip-rod installed.

In a fifteenth step S115, the cannula 300 is lifted off the inferior screw 710, and with the cannula 300 still in the surgical field, the space between superior screw 710 and inferior screw 810 is cleared out using forceps and the endoscope inserted through the cannula 300. Finally, the rod 830 is flipped down and lowered into the tulip 711 of the superior screw 710. Since the rod forms a ball-and-socket joint with the inferior screw 810, and the slots 716, 717, and 816 are aligned, the rod 830 may simply be pushed down into the tulip 711 of the superior screw 710 with endoscopic assistance. FIG. 14 shows a view of the rod 830 lowered into the superior screw 710.

Figure 15A:
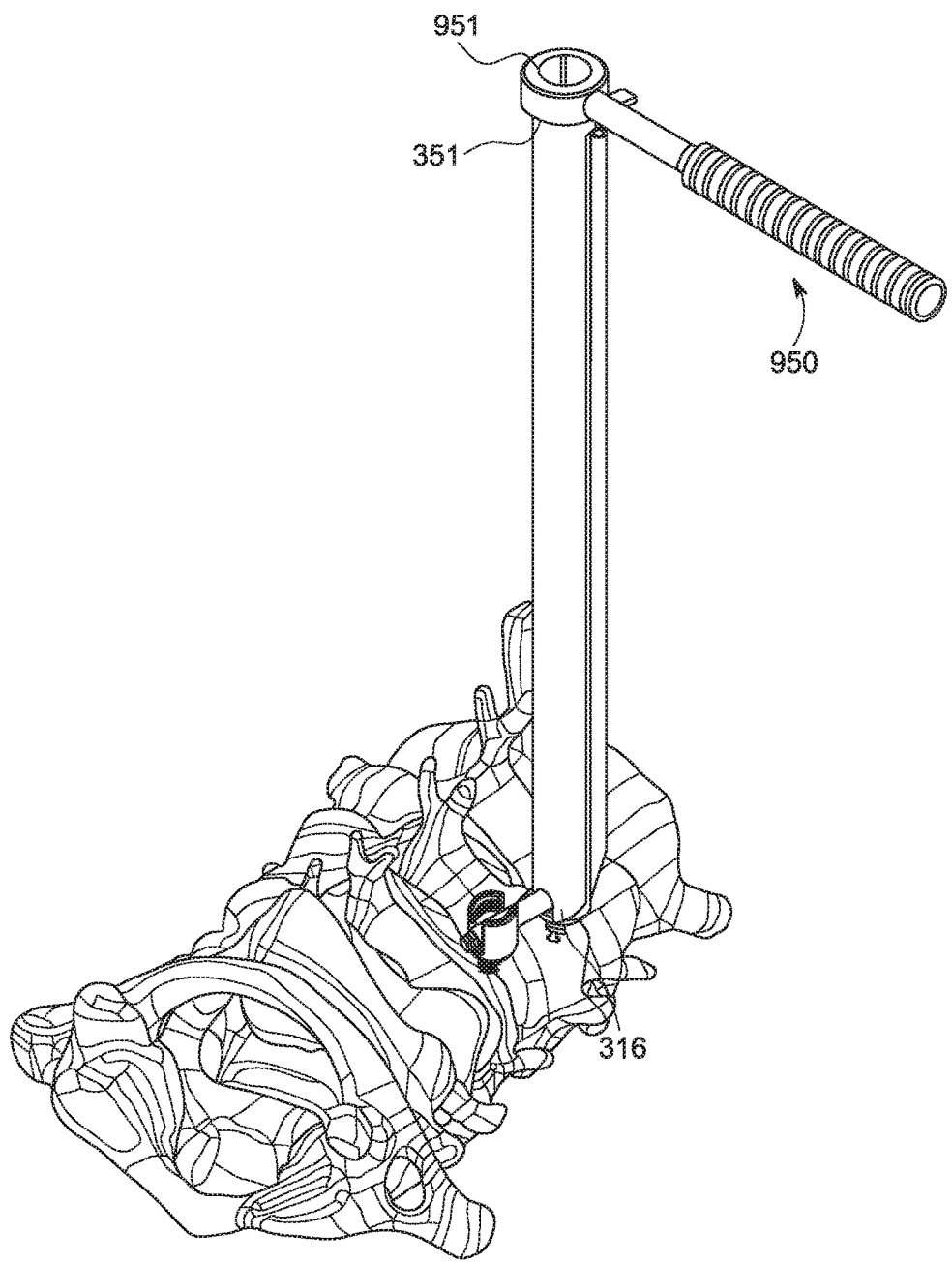
FIG. 15A is an isometric view of a section of cervical vertebrae with a counter torque handle attached to the access cannula.
Figure 15B:
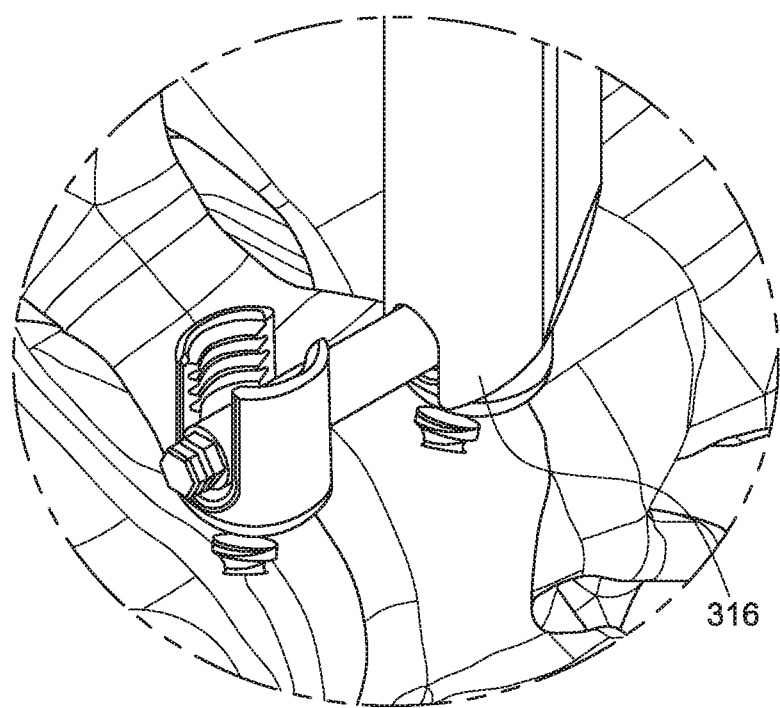
FIG. 15B is a close-up view of the counter torque feature engaging the rod.

In a sixteenth step S116, screw locking caps are installed as follows. First, as shown in FIG. 15A, the cannula 300 is again placed over one of the screws such that a slot 316 of the cannula engages the rod 830, as shown in detail in FIG. 15B. A counter torque handle 950 is attached to the cannula by means of mating features 951 and 351. This step can be first performed on either of the screws.

Figure 16A:
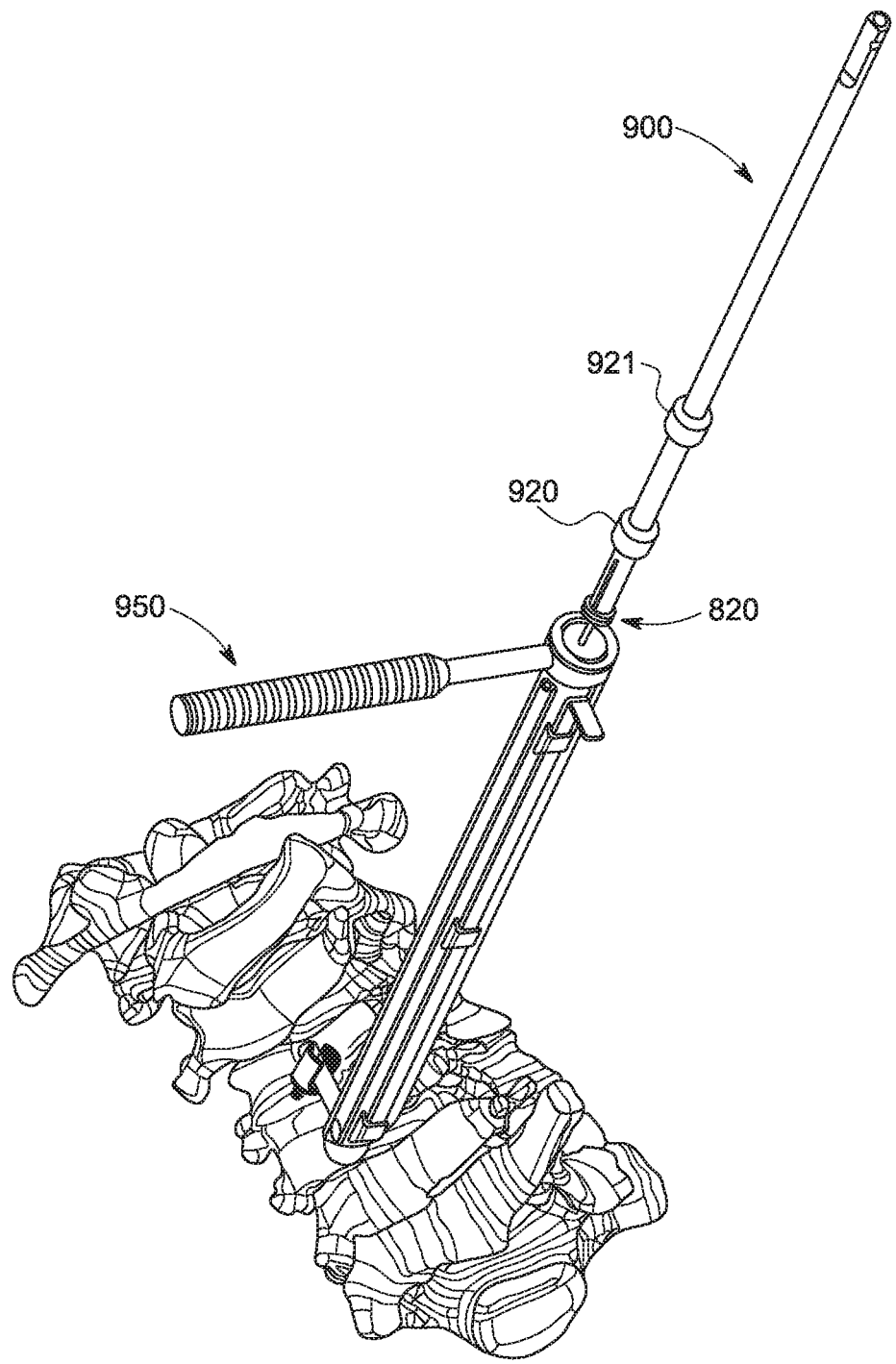
FIG. 16A is an isometric view of a section of cervical vertebrae with a final driver being inserted in the access cannula.
Figure 16B:
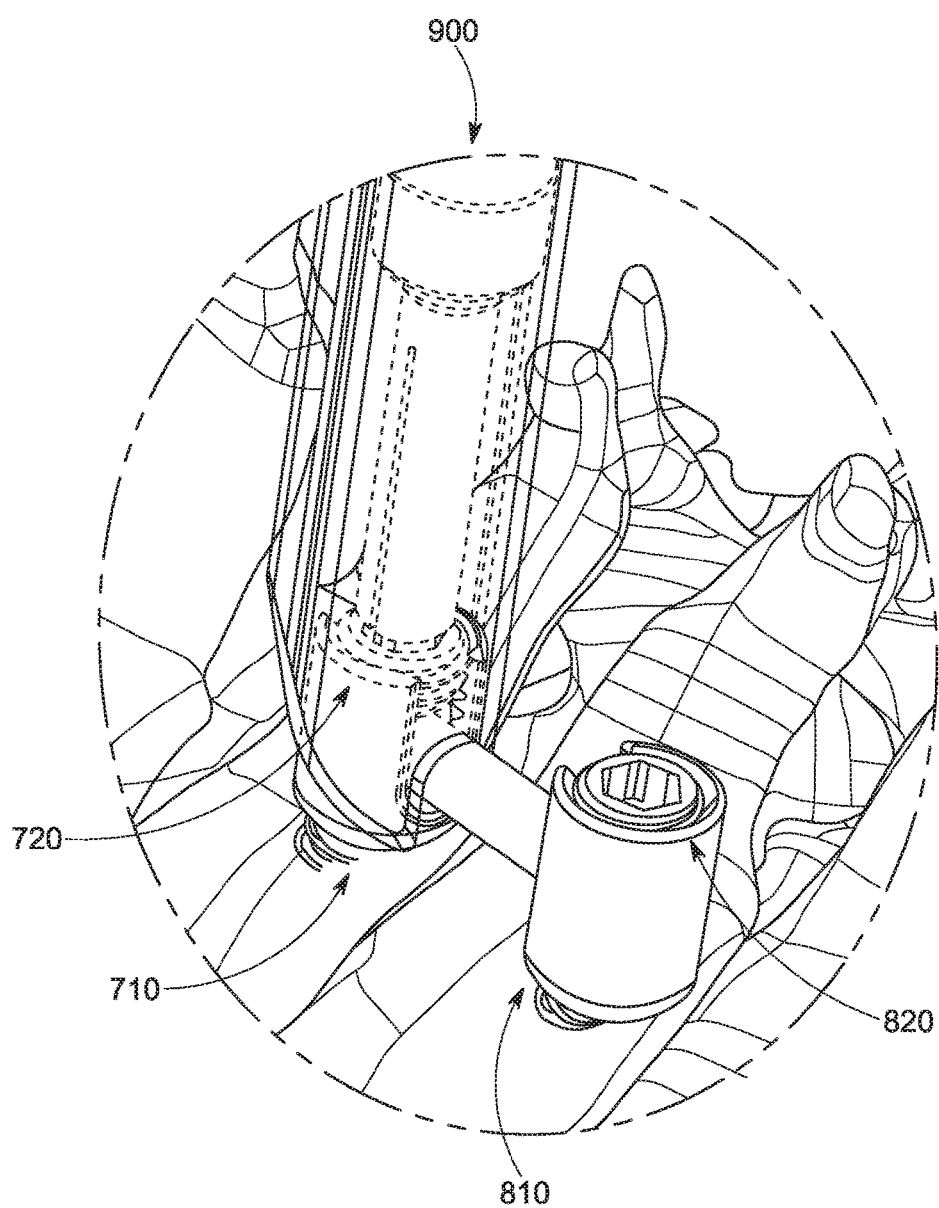
FIG. 16B is a close-up view of the final driver installing screw locking caps on the screw tulips.

Next, as shown in FIG. 16A and FIG. 16B, screw locking caps are placed and tightened on the screws. First locking cap 820 is inserted through the cannula 300 and screwed into tulip 811 using final driver 900. Like the other tools, the final driver has bushings 920 and 921 for maintaining a centralized position in the cannula 300. An end 911 of the final driver 900 mates with screw locking caps 820 and 720. After locking cap 820 is placed, the cannula 300 is repositioned and locking cap 720 is placed in a similar manner. The locking caps 820 and 720 are first installed provisionally, then finally. When tightening the locking caps 820 and 720, the counter torque handle 950 is used so that excessive torque is not directly applied to the screw assemblies and thus transmitted to the patient's spine. The locking cap 820 which fits over the ball 835 of the rod 830 is able to lock the rod 830 to the tulip 811 due to a semi-spherical coupling. For example, a bottom side of the locking cap 820 may have a semi-spherical concave shape while a top side is configured to mate with a screw driver. Similarly, the locking cap 720 which fits over an end of the rod 830 may have a bottom side configured to partially conform to the shape of the rod 830 for an optimal coupling.

According to the above exemplary procedure, an inferior screw assembly 800 and superior screw assembly 700 can be implanted into a patient. In a final configuration, the screws and rod are locked into place, as shown in FIG. 17.

According to the above exemplary procedure, various advantages may be obtained. For example, throughout the above procedure, the ability to use an endoscope placed through the cannula allows precise positioning of the surgical tools including the cannula in the surgical field. By using the above implants and instruments, a minimally invasive procedure can be accomplished. For example, in contrast to a conventional procedure in which tissue covering the vertebrae must be substantially removed, in an exemplary method of spinal fusion of this application only the tissue directly above the screw sites is displaced. Additionally, when lowering the flip-rod to connect two screws, tissue in between the screws need not be completely removed, but only displaced. The unique endoscopic procedure utilizing the access cannula described in exemplary embodiments avoids the need to open a wide surgical field.

Furthermore, only a single incision is needed to perform the implantation since the access cannula can be swept through a broad range of positions. It should be noted that the range of performing the procedure is only limited by the size of the incision. Therefore, when the site is small, for example when joining two vertebrae of the cervical spine, only one small incision may be required.

Next, it is also noted that the use of a rod having a ball at one end which forms a ball-and-socket joint with the tulip of one of the screws greatly enhances flexibility in aligning the two implanted screws. For example, when the above procedure is followed, there is no need to reposition the separate elements after their initial installation. Once the tulips are aligned, one can simply drop the rotatable rod down and fix the installation in its final position.

The materials of the implants, that is, the superior screw assembly 700 and the inferior screw assembly 800, should be selected from a material to ensure biocompatibility. For example, the implants may be titanium, or a titanium alloy. Other examples may include metal, plastic, ceramic, or a combination of materials.

In the above description, references to "inferior" and "superior" are merely exemplary, and it should be noted that the order of performing the implantation of "inferior" and "superior" screws can be reversed. Furthermore, although the "inferior" screw comprised the screw-rod in the above exemplary embodiment, it should be clear that the rod could be a part of the screw installed in the superior vertebra. The above exemplary procedure also demonstrates the implantation of a screw first and a screw-rod second, although this order can be reversed as well.

Furthermore, in another exemplary embodiment, three screws could be implanted. For example, one screw-rod having a rod that drops into the tulips of the two other screws to connect three vertebrae could be used. In this case, the above procedure may be appended by installing a third screw. As shown in FIG. 20, steps S104 through S109 can be repeated with another screw. It should be noted that the incision will be slightly larger, and the flip-rod will be longer in such a case of three or more screws.

Figure 21:
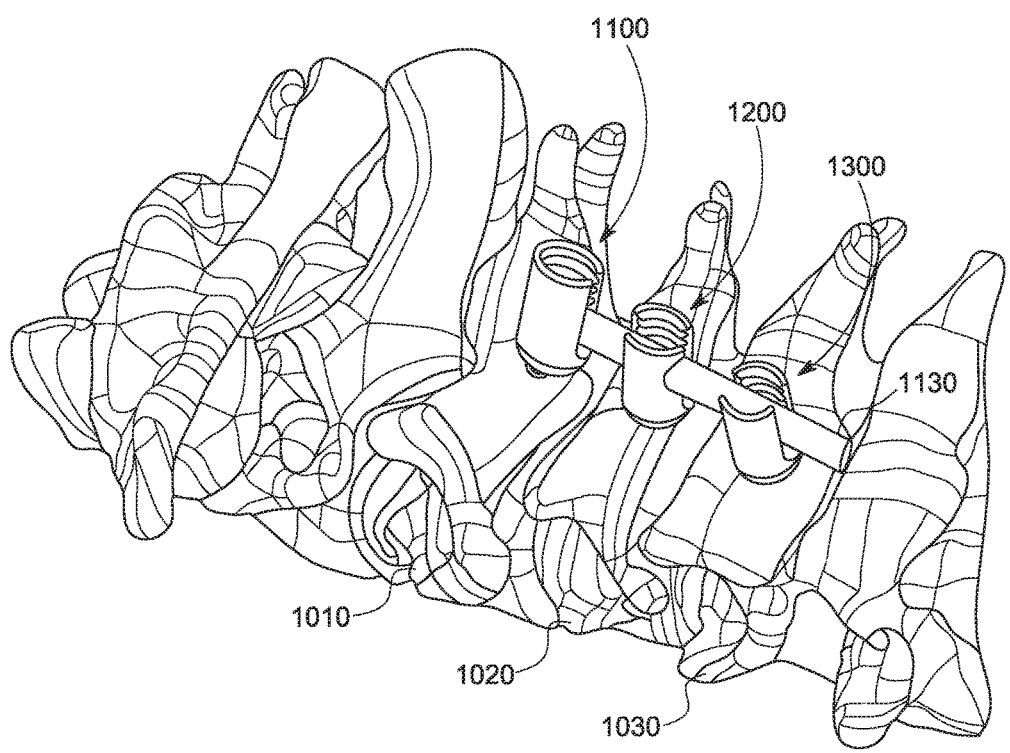
FIG. 21 is an isometric view of a section of cervical vertebrae with three screws and flip-rod installed.

Further details will be provided regarding a three-screw embodiment. When employing a three-screw arrangement, a rigid, straight rod can be used. However, since the spine is naturally curved, it is understood that the position and implantation depth of the screws will be varied to accommodate mating with a straight rod. For example, as shown in FIG. 21, three screws 1100, 1200, and 1300 are implanted at different angles and different depths in three adjacent vertebrae 1010, 1020, and 1030 so that the rod 1130 of the first screw 1100 can be flipped into place, engaging the tulips of the other two screws 1200 and 1300. The assembly shown in FIG. 21 is completed by installing locking caps in a manner similar to that described in the above exemplary embodiments.

As an alternative to a fixed straight rod, a rod having a joint or a hinge in the rod body could also be used. Using such a hinged rod, the rod is configured to be straight during insertion through the cannula. Then in the step of lowering the rod, the rod is bendable such that the rod can first be aligned with the tulip of one screw and then a section of the rod may pivot about the hinge to align with the tulips of one or more other screws. After being lowered into the tulips of the other screws, the hinge can be fixed by, for example, tightening a screw that locks the hinge into position.

As a further alternative in a three screw embodiment, two screw-rods may be placed at distal vertebrae of the three vertebrae to be joined. The two rods may then be lowered into one screw placed in the middle vertebra where they engage slots on respective sides on the one middle screw. The ends of the two rods may be joined and fixed together for added stability.

In the above manner, a plurality of screws beyond three could also be implanted.

Moreover, although the above exemplary embodiments have discussed spinal fusion systems and methods applied in the posterior cervical spine, the above systems and methods may also be applied in other parts of the vertebral column, for example the thoracic spine, and lumbar-sacral spine.

What is claimed is:

1. A spinal fusion apparatus comprising:
    a first screw assembly, wherein the first screw assembly comprises a shaft part and a tulip having a slot; and
    a second screw assembly, wherein the second screw assembly comprises a shaft part extending in an axial direction, a tulip having a slot, and a rod having a ball,
    wherein the ball is detachable from the shaft part of the second screw assembly, the ball is configured to form a pivot joint with the tulip of the second screw assembly, and the slot of the first screw assembly and the slot of the second screw assembly are configured to mate with the rod to thereby connect the first screw assembly and the second screw assembly by the rod, and
    the rod comprises one of a male part and a female part protruding in the axial direction and the shaft part of the second screw assembly comprises the other of the male part and the female part protruding in the axial direction, such that the rod is attachable to the shaft part of the second screw assembly, and the rod is configured to drive the shaft part of the second screw assembly;
    wherein the tulip of the second screw assembly comprises a threaded part,
    the spinal fusion apparatus further comprising a driver having a threaded part configured to couple with the threaded part of the tulip of the second screw assembly; and
    wherein a part of the rod is provided within an outer sleeve of the driver when the shaft part of the second screw assembly is being driven.

2. The spinal fusion apparatus of claim 1, wherein the rod comprises the ball at one end and a tip at another end, wherein the tip is configured to mate with a screw driver.

3. The spinal fusion apparatus of claim 2, wherein the tip of rod is configured to mate with the screw driver in a snap type latching connection.

4. The spinal fusion apparatus of claim 1, wherein the ball is configured to form a ball-and-socket joint with the tulip of the second screw assembly.

5. The spinal fusion apparatus of claim 1, wherein the tulip of the first screw assembly comprises a rounded lower surface configured to engage a rounded upper surface of a head of the shaft part of the first screw assembly.

6. The spinal fusion apparatus of claim 1, wherein the tulip of the second screw assembly comprises a rounded lower surface configured to engage a rounded upper surface of a head of the shaft part of the second screw assembly.

7. The spinal fusion apparatus of claim 1, further comprising
    a third screw assembly, wherein the third screw assembly comprises a shaft part and a tulip having a slot.

8. The spinal fusion apparatus of claim 6, wherein the tulip of the second screw assembly comprises a threaded part, the spinal fusion apparatus further comprising
    a driver having a threaded part configured to couple with the threaded part of the tulip of the second screw assembly and force the rounded lower surface of the tulip of the second screw assembly into press contact with the rounded upper surface of the head of the shaft part of the second screw assembly.

9. The spinal fusion apparatus of claim 1, wherein the driver comprises an outer sleeve having the threaded part and an inner shaft configured to drive the rod.

10. The spinal fusion apparatus of claim 1, wherein the rod comprises the ball at one end and a tip at another end, wherein the tip is configured to mate with an inner shaft of the driver, and
    the driver comprises an outer sleeve having the threaded part, the outer sleeve and the inner shaft being independently rotatable.

11. A screw assembly comprising
    a shaft part extending in an axial direction, a tulip having a slot, and a rod having a ball,
    wherein the ball is detachable from the shaft part of the screw assembly, the ball is configured to form a pivot joint with the tulip, and the slot of tulip is configured to mate with the rod to lock the screw assembly, and
    the rod comprises one of a male part and a female part protruding in the axial direction and the shaft part comprises the other of the male part and the female part protruding in the axial direction, such that the rod is attachable to the shaft part of the screw assembly, and the rod is configured to drive the shaft part of the screw assembly;

wherein the tulip of the second screw assembly comprises a threaded part, the spinal fusion apparatus further comprising a driver having a threaded part configured to couple with the threaded part of the tulip of the second screw assembly; and wherein a part of the rod is provided within an outer sleeve of the driver when the shaft part of the second screw assembly is being driven.

12. The screw assembly of claim 11, wherein the tulip comprises a rounded lower surface configured to engage a rounded upper surface of a head of the shaft part of the screw assembly.

13. The screw assembly of claim 12, wherein the tulip comprises a threaded part configured to mate with a driver having a threaded part and configured to couple with the threaded part of the tulip and force the rounded lower surface of the tulip into press contact with the rounded upper surface of the head of the shaft part.

* * * * *